(12) United States Patent
Rantanen

(10) Patent No.: US 12,343,125 B2
(45) Date of Patent: Jul. 1, 2025

(54) CARDIOVASCULAR HEALTH METRIC DETERMINATION FROM WEARABLE-BASED PHYSIOLOGICAL DATA

(71) Applicant: Oura Health Oy, Oulu (FI)

(72) Inventor: Antti Aleksi Rantanen, Oulu (FI)

(73) Assignee: Oura Health Oy, Oulu (FI)

( * ) Notice: Subject to any disclaimer, the term of this patent is extended or adjusted under 35 U.S.C. 154(b) by 165 days.

(21) Appl. No.: 17/818,105

(22) Filed: Aug. 8, 2022

(65) Prior Publication Data
US 2024/0041340 A1    Feb. 8, 2024

(51) Int. Cl.
*A61B 5/024*    (2006.01)
*A61B 5/00*    (2006.01)
(Continued)

(52) U.S. Cl.
CPC ...... *A61B 5/02438* (2013.01); *A61B 5/02007* (2013.01); *A61B 5/02416* (2013.01);
(Continued)

(58) Field of Classification Search
CPC ............ A61B 5/02007; A61B 5/02416; A61B 5/0261; A61B 5/0295; A61B 5/7264;
(Continued)

(56) References Cited

U.S. PATENT DOCUMENTS 10,709,339 B1 * 7/2020 Lusted .................. A61B 5/282
2013/0324859 A1   12/2013 Park et al.
(Continued)

FOREIGN PATENT DOCUMENTS

WO    WO-2021040292 A1 *  3/2021
WO    WO-2021249850 A1 * 12/2021

OTHER PUBLICATIONS

Wadstrom et al., "A Vascular Aging Index as Independent Predictor of Cardiovascular Events and Total Mortality in an Elderly Urban Population", Angiology 2019, vol. 70(10) 929-937 (Year: 2019).*
(Continued)

*Primary Examiner* — Boniface N Nganga
(74) *Attorney, Agent, or Firm* — Holland & Hart LLP

(57) ABSTRACT

Methods, systems, and devices for cardiovascular health metric determination are described. A system may be configured to receive a photoplethysmogram (PPG) signal representative of a pulse waveform for a user. The pulse waveform may include a first local maximum, a downward slope following the first local maximum, and a curved feature representative of a transition from a systolic phase to a diastolic phase of a cardiac cycle. Additionally, the system may extract one or more morphological features from the pulse waveform and compare the one or more morphological features with one or more features from a plurality of baseline PPG signal morphologies associated with a plurality of chronological ages. The system may determine a cardiovascular health metric that indicates a cardiovascular health of the user relative to a chronological age of the user and cause a graphical user interface to display an indication of the cardiovascular health metric.

19 Claims, 11 Drawing Sheets

(51) Int. Cl.
    *A61B 5/02*     (2006.01)
    *A61B 5/026*     (2006.01)
    *A61B 5/0295*     (2006.01)

(52) U.S. Cl.
    CPC .......... *A61B 5/0261* (2013.01); *A61B 5/0295* (2013.01); *A61B 5/486* (2013.01); *A61B 5/6802* (2013.01); *A61B 5/7239* (2013.01); *A61B 5/7246* (2013.01); *A61B 5/7264* (2013.01); *A61B 5/742* (2013.01)

(58) Field of Classification Search
    CPC . A61B 5/02438; A61B 5/6802; A61B 5/6826; A61B 5/7239; A61B 5/7246; A61B 5/7275
    See application file for complete search history.

(56) References Cited

U.S. PATENT DOCUMENTS

2021/0030372 A1*   2/2021   Lizio .................. A61B 5/02405
2022/0110547 A1*   4/2022   Kinnunen .......... A61B 5/02416
2023/0371827 A1   11/2023   Mitchell et al.

OTHER PUBLICATIONS

Ahn "New Aging Index Using Signal Features of Both Photoplethysmograms and Acceleration Plethysmograms", Healthc Inform Res. Jan. 2017;23(1):53-59. (Year: 2017).*

Charlton Peter H. et al. "Assessing hemodynamics from the photoplethysmogram to gain insights into vascular age: a review from VascAgeNet", American Journal of Physiology Heart and Circulatory Physiology, vol. 322, No. 4, Mar. 7, 2022.

Shin Hangsik et al: "Photoplethysmogram based vascular aging assessment using the deep convolutional neural network", Scientific Reports, vol. 12, No. 1, Jul. 5, 2022.

International Search Report and Written Opinion—PCT/US2023/071595—ISA/EPO—Oct. 26, 2023.

* cited by examiner

CARDIOVASCULAR HEALTH METRIC DETERMINATION FROM WEARABLE-BASED PHYSIOLOGICAL DATA

FIELD OF TECHNOLOGY

The following relates to wearable devices and data processing, including cardiovascular health metric determination from wearable-based physiological data.

BACKGROUND

Some wearable devices may be configured to collect data from users including photoplethysmogram (PPG) data, heart rate data, and the like. For example, some wearable devices may be configured to collect physiological data associated with the cardiovascular health of a user. However, wearable devices may be deficient in determining a cardiovascular health metric of the user.

DETAILED DESCRIPTION

Figure 1:
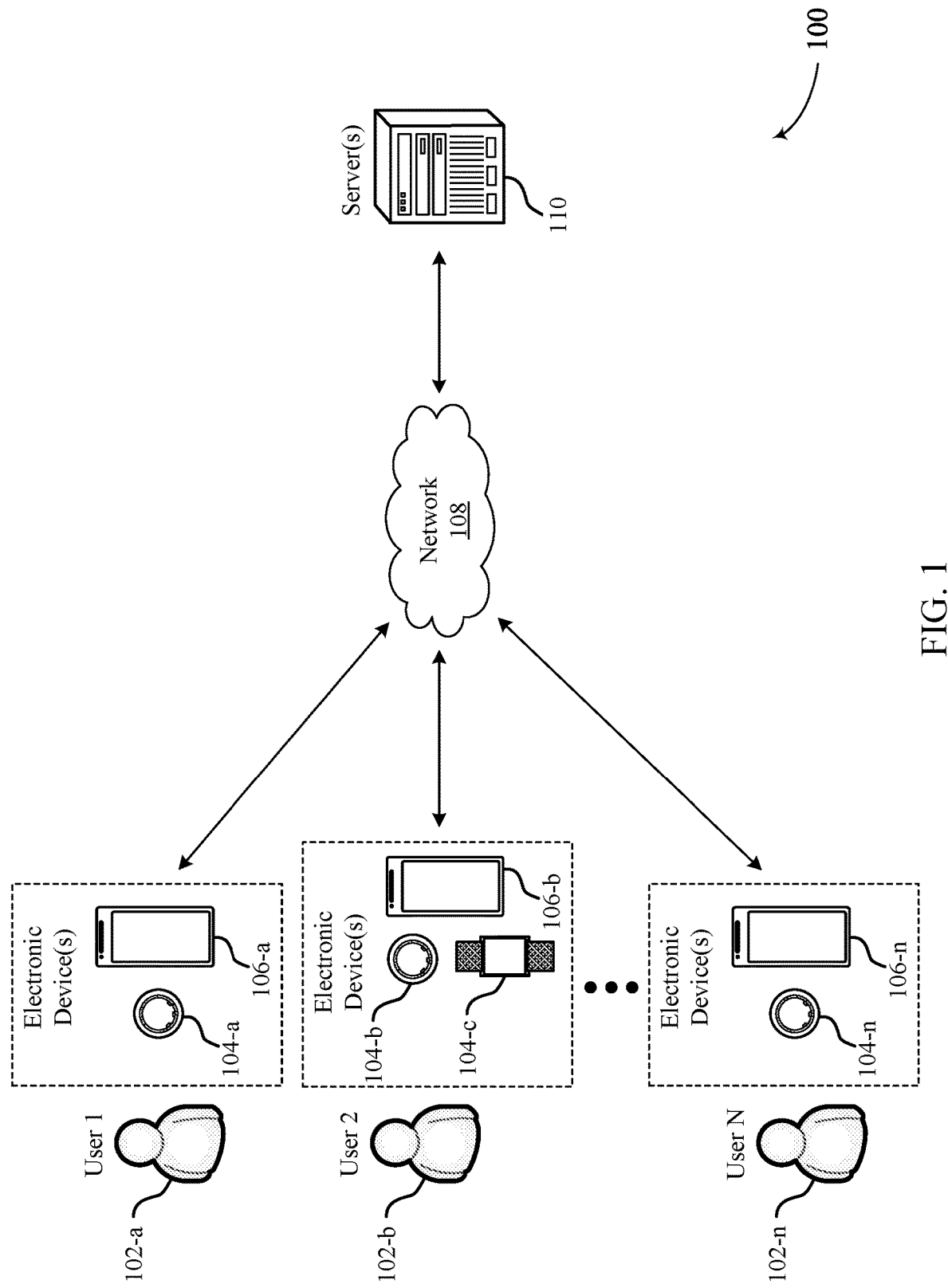
FIG. 1 illustrates an example of a system that supports cardiovascular health metric determination from wearable-based physiological data in accordance with aspects of the present disclosure.

Some wearable devices may be configured to collect physiological data from users, including photoplethysmogram (PPG) data, temperature data, heart rate, heart rate variability (HRV) data, sleep data, respiratory data, blood pressure data, and the like. Acquired physiological data may be used to analyze behavioral and physiological characteristics associated with the user, such as movement, and the like. Many users have a desire for more insight regarding their physical health, including their activity patterns and overall physical well-being. In particular, many users may have a desire for more insight regarding cardiovascular health, including their cardiovascular age, heart health, arterial stiffness, and risk for cardiovascular diseases include coronary heart disease, stroke, heart failure, heart arrhythmias, and the like. However, typical techniques to measure cardiovascular health and/or health devices and applications lack the ability to provide robust determination and insight for several reasons.

First, devices that record electrical signals of the heart and collect images of the heart and/or blood vessels may be obtained at a single instance and may be combined with other measurement techniques and calculations to determine the health of the cardiovascular system of the user. Second, even for devices that are wearable or that collects a user's physiological data, typical devices and applications lack the ability to collect other physiological, behavioral, or contextual inputs from the user that can be combined with the measured data to more comprehensively understand the complete set of physiological contributors to a user's cardiovascular health.

Aspects of the present disclosure are directed to techniques for determining a cardiovascular health metric from wearable-based physiological data. In particular, computing devices of the present disclosure may receive physiological data from the wearable device associated with the user. The physiological data may include at least a PPG signal representative of a pulse waveform for the user. Aspects of the present disclosure may identify morphological features of the pulse waveform including at least a first local maximum, a downward slope following the first local maximum, and a curved feature representative of a transition from a systolic phase to a diastolic phase of a cardiac cycle.

In some examples, aspects of the present disclosure may compare the identified morphological features of the pulse waveform with features of a plurality of PPG signal morphologies associated with a plurality of chronological ages. For example, the system may compare an individual pulse waveform to a typical pulse waveform with different age groups to identify which age group pulse waveform matches the individual pulse waveform. As such, aspects of the present disclosure may provide techniques for determining a cardiovascular health metric for the user based on the comparison, where the cardiovascular health metric indicates a cardiovascular health of the user relative to a chronological age of the user.

For the purposes of the present disclosure, the term "cardiovascular age metric," "cardiovascular health metric," or "cardiovascular age" and like terms, may be used to refer to a health metric of the user's cardiovascular system. The cardiovascular system may include the heart, blood vessels, and/or blood where the primary function of the cardiovascular system is to transport nutrients and oxygen-rich blood to all parts of the body and to carry deoxygenated blood back to the lungs. Cardiovascular age (e.g., heart age and/or vascular age) is a metric used to understand the user's risk for cardiovascular disease including heart attack or stroke. In some cases, the cardiovascular (e.g., heart) age may be calculated based on risk factors for heart disease such as age, blood pressure, and cholesterol, as well as diet, exercise, and smoking. Vascular age may provide a measure of the apparent age of the user's arteries.

In some cases, determining a cardiovascular health metric may reduce later-life health risks for users, specifically risks for cardiovascular diseases. In such cases, techniques to determine the cardiovascular health metric and provide recommendations for improving their cardiovascular health metric for users, in order to improve quality of life, sleep, and mood, and to reduce future health risks may be desired. For example, methods and techniques to help users understand in a personalized way how to optimize lifestyle changes to reduce the risk for cardiovascular disease may be desired. In such cases, the system may be able to determine a cardiovascular health metric relative to the chronological age of the user in order to provide metrics that may enable users to understand how behavior changes (e.g., improvements in sleep, exercise, diet, and mood) may help improve their cardiovascular health metric and reduce the risks for cardiovascular disease, and the like.

Techniques described herein may notify a user of the determined cardiovascular health metric in a variety of ways. For example, a system may cause a graphical user interface (GUI) of a user device to display a message or other notification to notify the user of the determined cardiovascular health metric, and make recommendations to the user. In one example, the system may generate recommendations for users about avoiding certain foods and/or drinks, intensifying the user's training, or building in more recovery time based on the cardiovascular health metric.

A GUI may also include graphics/text which indicate the data used to make the cardiovascular health metric. The system may also transmit a message to the user to confirm a change in the cardiovascular health metric. Based on the early warnings (e.g., before noticeable symptoms), a user may take early steps that may help reduce the severity of upcoming symptoms associated with a cardiovascular health metric that is greater than the chronological age of the user (e.g., symptoms associated with an onset of cardiovascular health issues). A GUI may also include graphics/text which reflects physiological changes associated with blood pressure, heart rate, and updating the recommendations to the user based on the physiological changes.

Aspects of the disclosure are initially described in the context of systems supporting physiological data collection from users via wearable devices. Additional aspects of the disclosure are described in the context of example timing diagrams and an example GUI. Aspects of the disclosure are further illustrated by and described with reference to apparatus diagrams, system diagrams, and flowcharts that relate to cardiovascular health metric determination from wearable-based physiological data.

FIG. 1 illustrates an example of a system 100 that supports cardiovascular health metric determination from wearable-based physiological data in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for determining a cardiovascular health metric from wearable-based physiological data. In particular, the system 100 illustrated in FIG. 1 may support techniques for determining a cardiovascular health metric that indicates a cardiovascular health of the user 102 relative to a chronological age of the user 102, and causing a user device 106 corresponding to the user 102 to display the indication of the cardiovascular health metric. The indication of a cardiovascular health metric may be based on a received PPG signal representative of a pulse waveform for the user 102 from a wearable device 104.

For example, as shown in FIG. 1, User 1 (user 102-*a*) may be associated with a wearable device 104-*a* (e.g., ring 104-*a*) and a user device 106-*a*. In this example, the ring 104-*a* may collect data associated with the user 102-*a*, including the PPG signal, temperature, heart rate, HRV, respiratory rate, and the like. In some aspects, data collected by the ring 104-*a* may be used to determine the cardiovascular health metric of the user 102 relative to the chronological age of the user 102. Determining the cardiovascular health metric may be performed by any of the components of the system 100, including the ring 104-*a*, the user device 106-*a* associated with User 1, the one or more servers 110, or any combination thereof. Upon determining the cardiovascular health metric, the system 100 may selectively cause the GUI of the user device 106 to display the indication of the cardiovascular health metric. In such cases, the user device 106 may be associated with User 1, User 2, User N, or a combination thereof where User 2 and User N may be an example of a clinician, a caregiver, a user associated with User 1, or a combination thereof.

In some implementations, upon receiving physiological data (e.g., including the PPG signal representative of the pulse waveform), the system 100 may extract one or more morphological features from the pulse waveform. For example, the pulse waveform may include a first local maximum, a downward slope following the first local maximum, and a curved feature representative of a transition from a systolic phase to a diastolic phase of a cardiac cycle. In such cases, the system 100 may extract one or more morphological features related to a position of the first local maximum, a value of the downward slope, a degree of the curved feature, or a combination thereof. It should be understood that additional or alternative morphological features of a pulse waveform may be used and that the examples listed are for illustrative purposes and should not be considered limiting. In some cases, the morphological features may be identified by a machine learning model and may represent complex combinations of features. The system 100 may compare the one or more extracted morphological features with one or more features from a plurality of baseline PPG signal morphologies associated with a plurality of chronological ages.

In some implementations, the system 100 may generate alerts, messages, or recommendations for User 1, User, 2, and/or User N (e.g., via the ring 104-*a*, user device 106-*a*, or both) based on the determined cardiovascular health metric, where the messages may provide insights regarding the determined cardiovascular health metric. In some cases, the messages may provide insights regarding symptoms associated with the cardiovascular health metric, educational videos and/or text (e.g., content) associated with the cardiovascular health metric loss, recommendations to improve the cardiovascular health metric, an adjusted set of activity and/or sleep targets, or a combination thereof.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
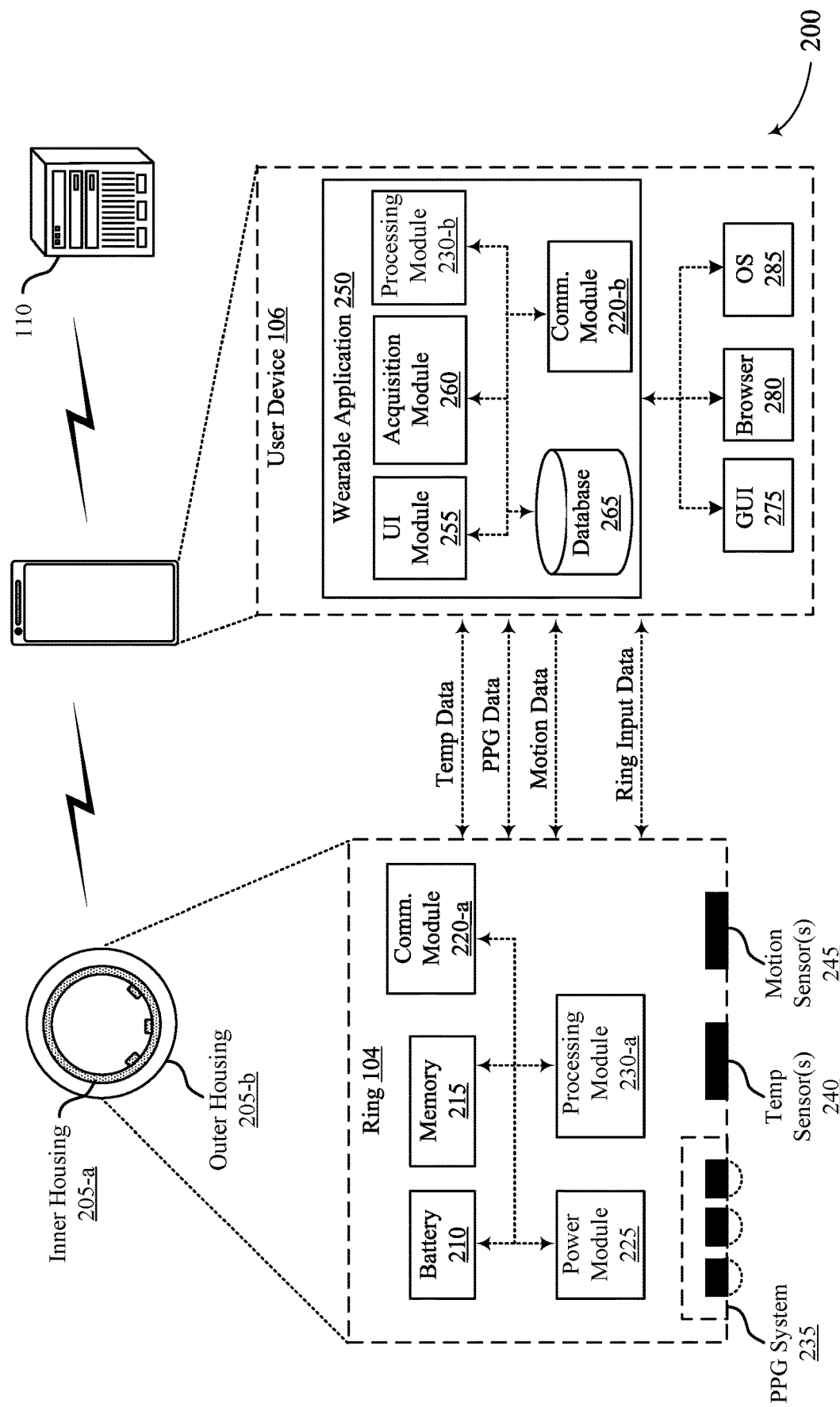
FIG. 2 illustrates an example of a system that supports cardiovascular health metric determination from wearable-based physiological data in accordance with aspects of the present disclosure.

FIG. 2 illustrates an example of a system 200 that supports cardiovascular health metric determination from wearable-based physiological data in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-b. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be preprocessed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for determining a cardiovascular health metric from wearable-based physiological data. In particular, the respective components of the system 200 may be used to determine a cardiovascular health metric that indicates a cardiovascular health of the user relative to a chronological age of the user based on comparing one or more morphological features of the user's pulse waveform with one or more features from a plurality of baseline PPG signal morphologies associated with a plurality of chronological ages. The indication of the cardiovascular health metric for the user may be determined by leveraging PPG sensors on the ring 104 of the system 200. In some cases, the indication of the cardiovascular health metric may be determined by identifying one or more morphological features of the PPG signal such as a position of the first local maximum, a value of the downward slope, a degree of the curved feature, or a combination thereof, in addition to other morphological features.

For example, as noted previously herein, the ring 104 of the system 200 may be worn by a user to collect data from the user, including the PPG signal, temperature, heart rate, HRV, respiratory data, and the like. The ring 104 of the system 200 may collect the physiological data from the user based on PPG sensors and measurements extracted from arterial blood flow (e.g., using PPG signals), capillary blood flow, arteriole blood flow, or a combination thereof. The physiological data may be collected continuously. In some implementations, the processing module 230-a may sample and/or receive the user's PPG signal continuously throughout the day and night. Sampling at a sufficient rate (e.g., one sample per second or one sample per minute) throughout the day and/or night may provide sufficient data for analysis described herein. In some implementations, the ring 104 may continuously acquire the PPG signal (e.g., at a sampling rate). In some examples, even though the PPG signal is collected continuously, the system 200 may leverage other information about the user that it has collected or otherwise derived (e.g., sleep stage, activity levels, illness onset, etc.) to select a representative PPG signal for a particular day that is an accurate representation of the underlying physiological phenomenon.

In contrast, systems that require a user to manually obtain their PPG signal each day and/or systems that acquire PPG signals continuously but lack any other contextual information about the user may select inaccurate or inconsistent PPG signals for their cardiovascular health metric determinations, leading to inaccurate determinations and decreased user experience. In contrast, data collected by the ring 104 may be used to accurately determine the cardiovascular health metric of the user. Determining the cardiovascular health metric and related techniques are further shown and described with reference to FIG. 3.

Figure 3:
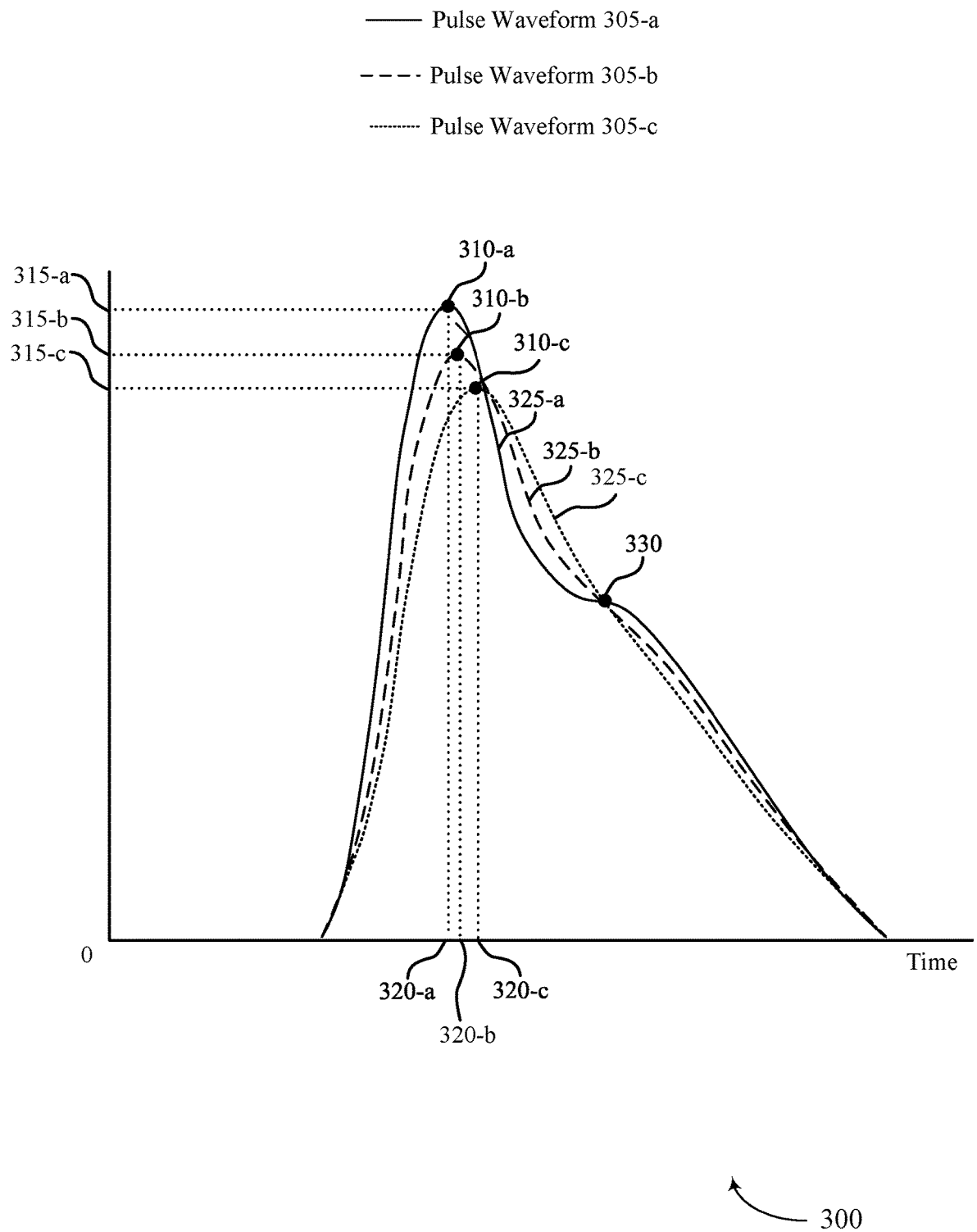
FIG. 3 illustrates an example of a timing diagram that supports cardiovascular health metric determination from wearable-based physiological data in accordance with aspects of the present disclosure.

FIG. 3 illustrates an example of a timing diagram 300 that supports cardiovascular health metric determination from wearable-based physiological data in accordance with aspects of the present disclosure. The timing diagram 300 illustrates a relationship between a pulse waveform 305 and time. In this regard, the solid curved line illustrated in the timing diagram 300 may be understood to refer to the "pulse waveform 305-a" that may be an example of the received pulse waveform of the user. The dashed curved lines illustrated in the timing diagram 300 may be understood to refer to "pulse waveforms 305-b and 305-c" that may be an example of baseline PPG signal morphologies. For example, the pulse waveform 305-b may be an example of a baseline PPG signal morphology for users between the ages of 40 and 44. The pulse waveform 305-c may be an example of a baseline PPG signal morphology for users between the ages of 65 and 70. As described in in more detail below, by comparing the received pulse waveform 305-a to baseline pulse waveforms associated with particular chronological ages (e.g., pulse waveforms 305-b or 305-c), a cardiovascular health metric may be determined, which may indicate how the user's cardiovascular health at their current chronological age compares to the baseline cardiovascular health of users of different chronological ages. For example, if a user is 60 years old, but their pulse waveform matches most closely (e.g., based on a comparison of one or more morphological features) with the baseline pulse waveform of a 30 year old, then the user may be assigned a relatively high cardiovascular health metric.

The pulse waveform 305-a may be generated and/or identified based on data that is extracted from the wearable device for a single user. For example, the system (e.g., ring 104, user device 106, server 110) may receive physiological data including at least the PPG signal for the user from the wearable device. The pulse waveform 305-a may be an example of the user's average pulse waveform taken over a plurality of days. The plurality of days may be example of at least twenty days (e.g., including at least twenty nights). In such cases, the system may estimate the cardiovascular health metric after receiving at least twenty nights of PPG signals. The system may average the received PPG signals taken over the plurality of days to be representative of a single pulse waveform for the user (e.g., the pulse waveform 305-a). In such cases, determining the average pulse waveform 305-a may omit outliers such as when the user is experiencing an illness, stress, or other factors that affect the PPG signal. Moreover, the system may omit or adjust a weighting of certain days of collected data based on other contextual information that is collected from the wearable device or the application, such as through tags, activity detection, location information, or the like.

The pulse waveforms 305-b and 305-c may be generated and/or identified based on data that is extracted from the wearable device for multiple users from multiple wearable devices. In such cases, the system may identify the plurality of baseline PPG signal morphologies (e.g., including the pulse waveforms 305-b and 305-c) associated with the plurality of chronological ages. For example, the system may receive PPG signals that may be paired with the multiple user's chronological age. In such cases, the multiple users may be categorized into different groups corresponding to the age of the user. For each subject (e.g., user) in the group, an average pulse waveform may be formed. For example, the average pulse waveform for each user within the group may be representative of PPG samples collected over the plurality of days (e.g., at least twenty nights). In some cases, the average pulse waveform 305-b and 305-c may each be generated from thirty averaged PPG samples of different users in each age group to represent a user's average pulse morphology for the corresponding age group. In some cases, a baseline PPG signal morphology (e.g., pulse waveforms 305-b and 305-c) may be generated for users with different genders. The baseline signal PPG morphologies may be identified in response to receiving the physiological data including at least the PPG signal for the user.

As described herein, features may be extracted from the template pulses (e.g., pulse waveforms 305-b and 305-c) and used as an age classifier for the user relative to the user's received pulse waveform 305-a. By comparing the features extracted from the user's average pulse (e.g., pulse waveform 305-a) with features from template pulses (e.g., pulse waveforms 305-b and 305-c), the system may estimate the cardiovascular health metric of the user.

The system may process PPG signals to determine the cardiovascular health metric. The PPG signals may be continuously collected by the wearable device. The physiological measurements may be taken continuously throughout the day and/or night. For example, in some implementations, the ring may be configured to acquire physiological data (e.g., PPG signals and the like) continuously in accordance with one or more measurement periodicities throughout the entirety of each day/sleep day. In other words, the ring may continuously acquire physiological data from the user without regard to "trigger conditions" for performing such measurements.

The PPG signals may be used to generate a pulse waveform 305. The pulse waveform 305 may be an example of an arterial pulse waveform. In such cases, the arterial pulse waveform may be representative of a wave of rhythmic arterial pressure perceived by palpating an artery. In some cases, the arterial pulse waveform may be caused by the increase in blood pressure, ejected by the left ventricle of the heart into the aorta and the arteries. The pulse waveform 305 may include a systolic portion and a diastolic portion. The transition point between the systolic portion and the diastolic portion may manifest itself in a waveform as a notch or curved feature, and may be referred to as a dicrotic notch. The pulse waveforms 305 may each include a local maximum 310, a downward slope 325 following the local maximum 310, a curved feature 330 representative of a transition from the systolic portion to the diastolic portion, or a combination thereof. The local maximum 310 may be an example of a systolic peak of the systolic portion, and the dicrotic notch may be an example of the curved feature 330 representative of a transition from the systolic portion to the diastolic portion. The local maximum 310, downward slope 325 following the local maximum 310, and a curved feature 330 may be examples of features (e.g., morphological features) of the pulse waveforms 305.

In some cases, the amplitude 315-c of the local maximum 310-c for the pulse waveform 305-c may be lower than the amplitude 315-b of the local maximum 310-b for the pulse waveform 305-b. The position 320-c of the local maximum 310-c for the pulse waveform 305-c may be shifted (e.g., to the right) as compared to the position 320-b of the local maximum 310-b for the pulse waveform 305-b. In some examples, a second local maximum may be absent from the pulse waveform 305-c and/or the pulse waveform 305-b. The second local maximum may be an example of the curved feature 330 representative of a transition from the systolic portion to the diastolic portion. The amplitude 315 of the local maximum 310 may decrease with age, the position 320 of the local maximum 310 may shift to the right with age, the downward slope 325 may increase with age, the curved feature 330 may diminish with age, or a combination thereof. For example, the shape of the pulse waveform 305 may become more triangular with age. In such cases, the pulse waveform 305-c may correspond to an older chronological age than the pulse waveform 305-b, and the pulse waveform 305-b may correspond to an older chronological age than the pulse waveform 305-a.

The system may extract morphological features of the pulse waveform 305-a. The morphological features may be an example of the position 320-a of the local maximum 310-a, a value of the downward slope 325-a, a degree of the curved feature 330, or a combination thereof. In some cases, the system may extract features from the pulse waveforms 305-b and 305-c. The features may be an example of the position 320-b of the local maximum 310-b, the position 320-c of the local maximum 310-c, a value of the downward slope 325-b, a value of the downward slope 325-c, a degree of the curved feature 330, or a combination thereof.

In some cases, the system may determine, or identify, the local maximum 310-a for the pulse waveform 305-a. The system may identify the one or more downward slopes 325-a based on determining the local maximum 310-a. For example, the system may identify one or more downward slopes 325-a of the pulse waveform 305-a after receiving the PPG signal and prior to extracting the morphological feature related to the value of the downward slope 325-a. In some cases, the system may identify one or more upward slopes of the pulse waveform 305-a. The downward slope 325-a may be an example of a negative slope, and the upward slope may be an example of a positive slope. In some examples, the system may identify a presence of a second local maximum (e.g., representative of the curved feature 330) of the pulse waveform 305-a. In addition to these examples, or alternatively, the system may identify other morphological features of the pulse waveforms 305 using a number of statistical methods including machine learning (e.g., unsupervised learning) techniques.

The system may compare the features of the pulse waveform 305-a with the features of the pulse waveform 305-b, the pulse waveform 305-c, or any number of other baseline pulse waveforms 305. In some cases, the system may execute the comparison after extracting the features of the pulse waveform 305-a. For example, the system may compare the amplitude 315-a, the position 320-a, or both of the local maximum 310-a with the amplitude 315-b, the position 320-b, or both of the local maximum 310-b. In other examples, the system may compare the amplitude 315-a, the position 320-a, or both of the local maximum 310-a with the amplitude 315-c, the position 320-c, or both of the local maximum 310-c. In such cases, the system may determine that the amplitude 315-a of the local maximum 310-a is greater than the amplitudes 315-b and 315-c of the local maximums 310-b and 310-c, respectively. The system may determine that the position 320-a of the local maximum 310-a is to the left of the positions 320-b and 320-c of the local maximums 310-b and 310-c, respectively.

In some examples, the system may compare a value of the downward slope 325-a with the value of the downward slopes 325-b and 325-c. In such cases, the system may determine that the value of the downward slope 325-a is less than the value of the downward slopes 325-b and 325-c of the pulse waveforms 305-b and 305-c, respectively. The system may compare the degree of the curved feature 330 of the pulse waveform 305-a to the degree of the curved feature 330 of the pulse waveforms 305-b and 305-c. In some cases, the curved features 330 may be absent from the pulse waveforms 305-b and 305-c. In such cases, the degree of the curved feature 330 of the pulse waveform 305-a may be greater than the degree of the curved feature 330 of the pulse waveforms 305-b and 305-c.

In response to comparing the features of the pulse waveform 305-a with the features from the pulse waveform 305-b, the pulse waveform 305-c, or both, the system may determine a cardiovascular health metric that indicates a cardiovascular health of the user relative to a chronological age of the user. In some cases, the system may determine which of the baseline pulse waveforms 305 matches most closely with the pulse waveform 305-a. For example, system may determine that the pulse waveform 305-a may match a pulse waveform 305 (e.g., baseline PPG signal morphology) for a user between the chronological age of 20 and 24. In such cases, the system may determine that the cardiovascular health metric for the user corresponds to a cardiovascular health metric (e.g., cardiovascular age) of a user with the chronological age between 20 and 24.

The system may determine that the cardiovascular health metric for a user indicates a cardiovascular health that is less than or greater than the chronological age of the user. For example, the system may determine, based on the comparison, that the cardiovascular health metric of the user corresponds to a chronological age between 20 and 24 while the user's chronological age is 30, thereby indicating that the cardiovascular health of the user is healthy (e.g., in a normal or optimal range). In other examples, the system may determine that the cardiovascular health metric that indicates the cardiovascular health of the user is greater than the chronological age of the user. For example, the system may determine, based on the comparison, that the cardiovascular health metric of the user corresponds to a chronological age between 40 and 44 while the user's chronological age is 30, thereby indicating that the cardiovascular health of the user is unhealthy (e.g., in a sub-optimal range). In such cases, the system may provide recommendations to improve the cardiovascular health metric, as described with reference to FIG. 5.

Figure 4:
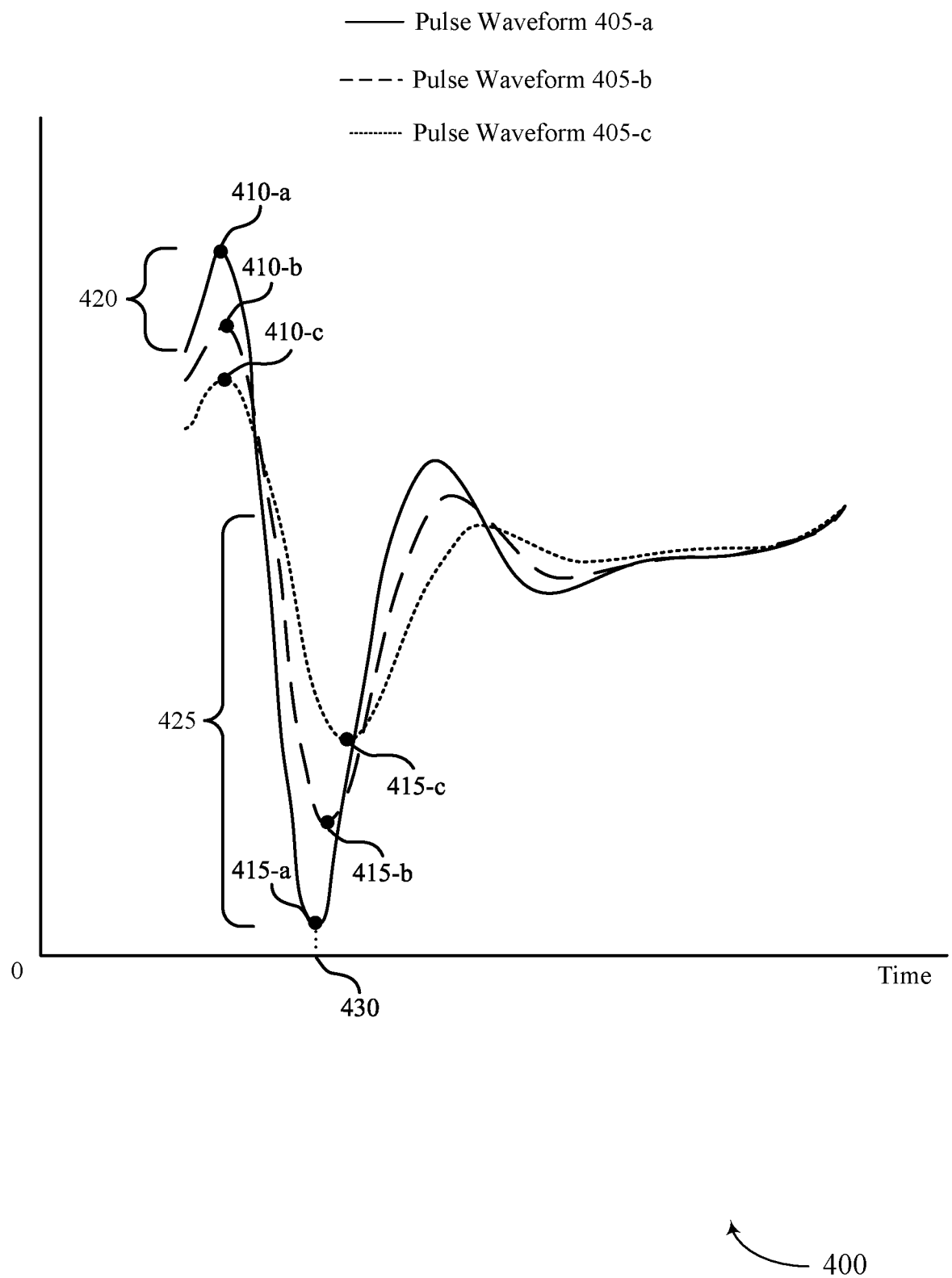
FIG. 4 illustrates an example of a timing diagram that supports cardiovascular health metric determination from wearable-based physiological data in accordance with aspects of the present disclosure.

FIG. 4 illustrates an example of a timing diagram 400 that supports cardiovascular health metric determination from wearable-based physiological data in accordance with aspects of the present disclosure. The timing diagram 400 illustrates a relationship between a second derivative pulse waveform 405 and time. In this regard, the solid curved line illustrated in the timing diagram 400 may be understood to refer to the "second derivative pulse waveform 405-a" which may be an example of a second derivative of the pulse waveform 305-a as described with reference to FIG. 3. The dashed curved lines illustrated in timing diagram 400 may be understood to refer to "second derivative pulse waveforms 405-b and 405-c" which may be examples of a second derivative of the pulse waveforms 305-b and 305-c, respectively.

In some cases, the system may compute and/or determine a first derivative of the original pulse waveforms (e.g. pulse waveforms 305 as described with reference to FIG. 3). In examples, the system may compute and/or determine a second derivative of the original pulse waveforms. The computed second derivatives of the pulse waveforms may be an example of the second derivative pulse waveforms 405. The system may identify one or more local maximum 410, one or more local minimum 415, or both of the second derivative pulse waveforms 405. In some cases, the system may identify one or more local maximum, one or more local minimum 415, or both of the first derivative pulse waveforms.

In some examples, the system may compare the second derivative pulse waveform 405-*a* (e.g., the second derivative of the received pulse waveform) with the second derivative pulse waveforms 405-*b* and 405-*c* (e.g., baseline PPG signal morphologies). For example, the system may determine that the local maximum 410-*a* of the second derivative pulse waveform 405-*a* may be greater than the local maximums 410-*b* and 410-*c* of the second derivative pulse waveforms 405-*b* and 405-*c*, respectively. The system may determine that the local minimum 415-*a* of the second derivative pulse waveform 405-*a* may be greater than the local minimum and 415-*b* and 415-*c* of the second derivative pulse waveforms 405-*b* and 405-*c*, respectively. In such cases, the system may compute a deviation in the features of the second derivative pulse waveform 405-*a* relative to the features of the second derivative pulse waveforms 405-*b* and 405-*c*. For example, the deviations in the second derivative pulse waveforms 405 may indicate a deviation in the original pulse waveforms.

As described with reference to FIG. 3, the cardiovascular health metric may be determined based on the comparison of the features (e.g., amplitude 425 and/or position of the local maximum 410-*a*, amplitude 425 and/or position 430 of the local minimum 415-*a*, or a combination thereof) of the second derivative pulse waveform 405-*a* with the features of the second derivative pulse waveforms 405-*b* and 405-*c*. The features of the second derivative pulse waveforms 405-*b* and 405-*c* may be an example of an amplitude and/or position of the local maximums 410-*b* and 410-*c*, amplitude and/or position of the local minimums 415-*b* and 415-*c*, or a combination thereof.

The system may determine the amplitude 420 of the local maximum 410-*a* second derivative pulse waveform 405-*a*. The amplitude 420 of the local maximum 410-*a* may be an example of a positive amplitude. In some cases, the amplitude 420 of the second derivative pulse waveform 405-*a* may be indicative of the cardiovascular health metric. In such cases, the system may determine the cardiovascular health metric based on identifying the local maximum 410-*a* and/or determining the amplitude 420 of the local maximum 410-*a*. For example, the system may determine the cardiovascular health metric in response to computing the first derivative of the pulse waveform, computing the second derivative pulse waveform 405-*a*, or both.

In some cases, the system may determine the amplitude 425 of the local minimum 415-*a* of the second derivative pulse waveform 405-*a*. The amplitude 425 of the local minimum 415-*a* may be an example of a negative amplitude. In some cases, the amplitude 425 of the local minimum 415-*a* may be indicative of the cardiovascular health metric. In such cases, the system may determine the cardiovascular health metric based on identifying the local minimum 415-*a* and/or determining the amplitude 425 of the local minimum 415-*a*. In some cases, the system may determine the position 430 (e.g., location) of the local minimum 415-*a*. In some cases, the position 430 of the local minimum 415-*a* may be indicate of the cardiovascular health metric. In such cases, the system may determine the cardiovascular health metric based on determining the position 430 of the local minimum 415-*a*.

The second derivative pulse waveforms 405 may include features that correlate with chronological age. For example, the amplitude 420 of the local maximum 410-*a* may decrease with chronological age, the amplitude 425 of the local minimum 415-*a* may decrease with chronological age, and the position of the local minimum 415-*a* may increase (e.g., shift to the right) with chronological age. In some cases, each age group may include a variation of cardiovascular health metrics. For example, the age group between 30 and 34 may include cardiovascular health metrics that indicate a cardiovascular age less than 30 and 34 and/or greater than 30 and 34.

In some cases, the system may determine a cardiovascular health index in response to determining the cardiovascular health metric. In such cases, the cardiovascular health index may include the cardiovascular health metric as a component as well as other inputs. The system may determine an arterial stiffness in response to determining the cardiovascular health metric. In such cases, the cardiovascular health index may be determined in response to determining the arterial stiffness. In some cases, the arterial stiffness may be based on the user's blood pressure. In some examples, the system may determine the cardiovascular health index based on cardiovascular health metric, arterial stiffness, blood pressure, resting heart rate, HRV, or a combination thereof.

Figure 5:
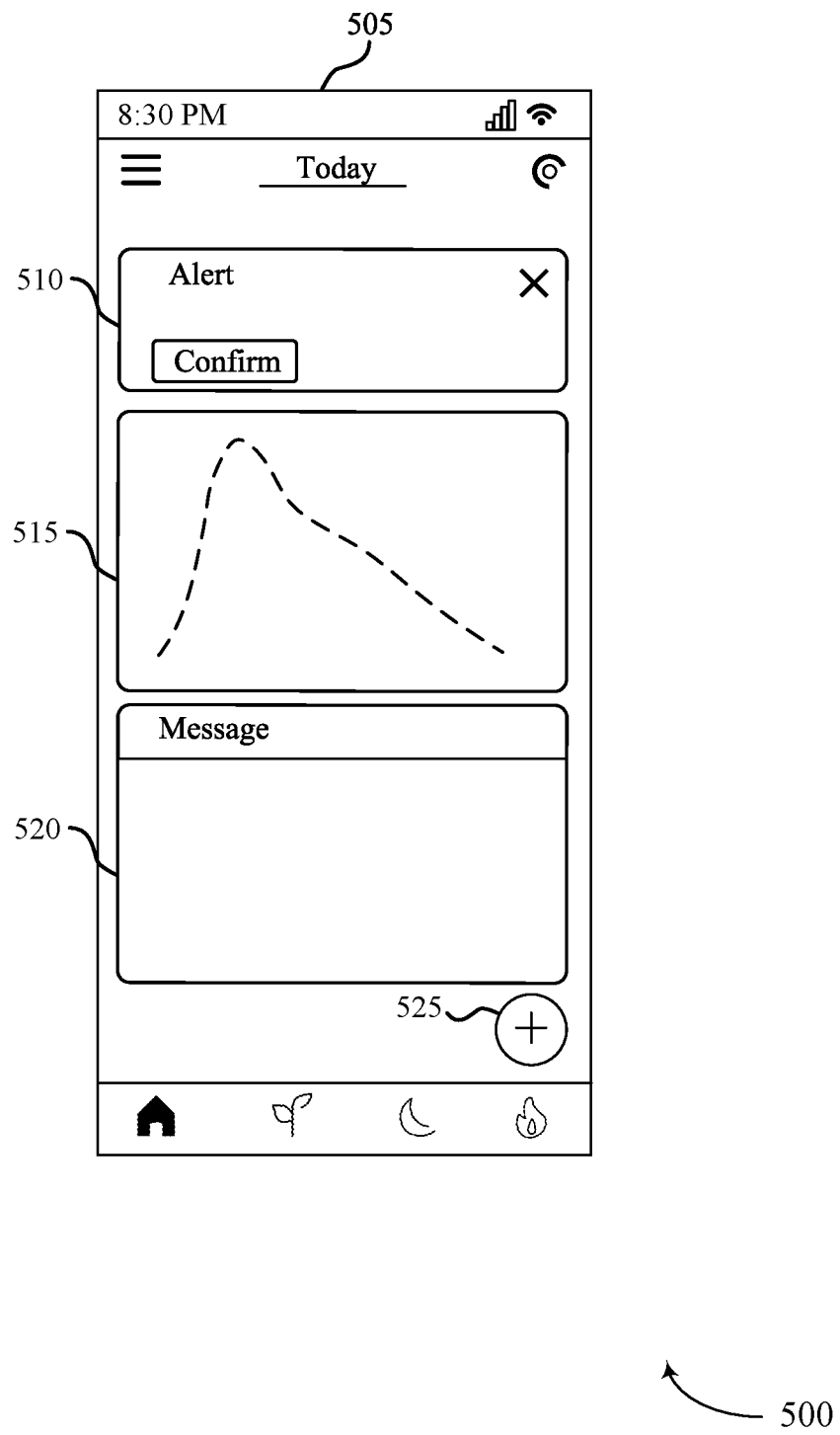
FIG. 5 illustrates an example of a graphical user interface (GUI) that supports cardiovascular health metric determination from wearable-based physiological data in accordance with aspects of the present disclosure.

FIG. 5 illustrates an example of a GUI 500 that supports cardiovascular health metric determination from wearable-based physiological data in accordance with aspects of the present disclosure. The GUI 500 may implement, or be implemented by, aspects of the system 100, system 200, timing diagram 300, timing diagram 400, or any combination thereof. For example, the GUI 500 may be an example of a GUI 275 of a user device 106 (e.g., user device 106-*a*, 106-*b*, 106-*c*) corresponding to a user 102. In some examples, the GUI 500 illustrates a series of application pages 505 which may be displayed to a user via the GUI 500 (e.g., GUI 275 illustrated in FIG. 2).

The server of the system may generate a message 520 for display on the GUI 500 on a user device that indicates the indication of the cardiovascular health metric. For example, the server of system may cause the GUI 500 of the user device (e.g., mobile device) to display a message 520 associated with the indication of the cardiovascular health metric (e.g., via application page 505). In such cases, the system may output the indication of the cardiovascular health metric on the GUI 500 of the user device to indicate a cardiovascular health of the user relative to a chronological age of the user.

Upon determining the indication of the cardiovascular health metric of the user, the user may be presented with the application page 505 upon opening the wearable application. As shown in FIG. 5, the application page 505 may display the indication that the cardiovascular health metric is determined and/or identified via message 520. In such cases, the application page 505 may include the message 520 on the home page. In cases where a user's cardiovascular health metric is determined and/or identified, as described herein, the server may transmit a message 520 to the user, where the message 520 is associated with the cardiovascular health metric. In some cases, the server may transmit a message 520 to a clinician, a care-taker, a partner of the user, or a combination thereof. In such cases, the system may present application page 505 on the user device associated with the clinician, the care-taker, the partner, or a combination thereof.

For example, the user may receive message 520, which may indicate trends associated with the cardiovascular health metric, educational content associated with the cardiovascular health metric, an adjusted set of sleep targets, an adjusted set of activity targets, recommendations to improve the cardiovascular health metric, and the like. The messages

520 may be configurable/customizable, such that the user may receive different messages 520 based on the determination of the cardiovascular health metric, as described previously herein.

In some cases, the message 520 may include weekly or monthly reports associated with the determined cardiovascular health metric. The reports may indicate the trends associated with the cardiovascular health metric. For example, the trends may indicate if the cardiovascular health metric is changing (e.g., increasing or decreasing) relative to the previously determined cardiovascular health metric. In some cases, the system may provide personalized recommendations to improve or maintain the cardiovascular health metric. For example, the message 520 may indicate "Did you know that exercising four times a week can impact your cardiovascular health metric? Try adding in some exercise this week."

In such cases, the message 520 may includes insights, recommendations, and the like associated with the determined cardiovascular health metric. The server of system may cause the GUI 500 of the user device to display a message 520 associated with the cardiovascular health metric. The user device may display recommendations and/or information associated with the cardiovascular health metric via message 520. As noted previously herein, an accurately determined cardiovascular health metric may be beneficial to a user's overall health.

Additionally, in some implementations, the application page 505 may display one or more scores (e.g., Sleep Score, Readiness Score, Activity Score, etc.) for the user for the respective day. Moreover, in some cases, the determined cardiovascular health metric may be used to update (e.g., modify) one or more scores associated with the user (e.g., Sleep Score, Readiness Score, etc.). That is, data associated with the cardiovascular health metric may be used to update the scores for the user for the following calendar days. In such cases, the system may notify the user of the score update via alert 510.

In some cases, the Readiness Score may be updated based on the cardiovascular health metric. In such cases, the Readiness Score may indicate to the user to "pay attention" based on the determined cardiovascular health metric. If the Readiness Score changes for the user, the system may implement a recovery mode for users whose symptoms associated with their cardiovascular health may be severe and may benefit from adjusted activity and readiness guidance for a couple of days, weeks, or months.

In other examples, the system may determine that the determined cardiovascular health metric (e.g., cardiovascular age) of the user is less than or equal to the chronological age of the user and may adjust the Readiness Score, Sleep Score, and/or Activity Score to accommodate the equal to (e.g., expected) or lower cardiovascular health metric. In other cases, the system may determine that the determined cardiovascular health metric (e.g., cardiovascular age) of the user is greater than the chronological age of the user and may adjust the Readiness Score, Sleep Score, and/or Activity Score to offset the effects of the higher cardiovascular health metric. In some cases, the system may provide insights to maintain the user's cardiovascular age (e.g., cardiovascular health metric) at an age lower than or the same as the user's chronological age. For example, the system may display, via message 520, recommendations and/or motivations for healthy habits and provide behavioral insights to the users.

In some cases, the messages 520 displayed to the user via the GUI 500 of the user device may indicate how the determined cardiovascular health metric affected the overall scores (e.g., overall Readiness Score) and/or the individual contributing factors. For example, a message 520 may indicate "It looks like your cardiovascular health metric is greater than your chronological age, but if you're feeling ok, doing a light or medium intensity exercise can improve your cardiovascular health metric" or "From your cardiovascular health metrics it looks like your right on track with your chronological age. Keep up the great work!" In cases where the cardiovascular health metric is determined, the messages 520 may provide suggestions for the user in order to improve their general health (e.g., including their cardiovascular health metric). In such cases, the messages 520 displayed to the user may provide targeted insights to help the user adjust their lifestyle.

The application page 505 may indicate one or more parameters, including the pulse waveform (e.g., a portion of the PPG signal), a temperature, heart rate, HRV, respiratory rate, sleep data, and the like via the graphical representation 515. The graphical representation 515 may be an example of the timing diagram 300 or timing diagram 400 as described with reference to FIGS. 3 and 4. In such cases, the system may cause the GUI 500 of a user device to display a message 520, alert 510, or graphical representation 515 associated with the cardiovascular health metric.

In some cases, the user may log symptoms or events via user input 525. For example, the system may receive user input (e.g., tags) to log symptoms and/or events associated with illness, stress, pregnancy, or the like. For example, the system may receive an indication, via user input 525, of data related to a health record of the user. The data related to the health record of the user may include the indication of illness, stress, pregnancy, alcohol use, exercise history, sleep habits, current medications, previous surgeries, and the like. In other examples, the system may receive the indication of the data related to the health record of the user from the wearable device, physiological data from the wearable device, or both. The physiological data from the wearable device may be an example of temperature, heart rate, HRV, respiratory rate, sleep data, blood pressure, and the like.

In such cases, the system may adjust the cardiovascular health metric in response to receiving the indication. For example, the cardiovascular health metric may be adjusted based on a medical history of the patient, physiological data obtained from the wearable device, or both. The system may cause the GUI 500 to display the indication (via alert 510, graphical representation 515, and/or message 520) based on adjusting the cardiovascular health metric. In such cases, the system may adjust the insights, recommendations, and the like based on the adjusted cardiovascular health metric. For example, the system may indicate "It looks like you may be experiencing a cold. Your cardiovascular health metric is higher than usual, but this will all balance out after you recover from your cold. Take some time to rest." In some examples, the system may indicate "Based on your healthy lifestyle, your cardiovascular health metric is below your chronological age. Keep up the great work!"

As shown in FIG. 5, the application page 505 may display the indication of the cardiovascular health metric via alert 510. In some cases, the application page 505 may display the indication of the adjusted cardiovascular health metric via alert 510. The user may receive alert 510, and the application page 505 may prompt the user to confirm or dismiss the determined cardiovascular health metric or the adjusted cardiovascular health metric. For example, the system may receive, via a user device and in response to adjusting the cardiovascular health metric, a confirmation of the cardiovascular health metric.

In some implementations, the system may provide additional insight regarding the user's determined cardiovascular health metric. For example, the application pages 505 may indicate one or more physiological parameters (e.g., contributing factors) which resulted in the user's determined cardiovascular health metric, such as deviations in the one or more morphological features relative to the one or more features from the baseline PPG signal morphologies, exercise habits, sleep habits, and the like. In other words, the system may be configured to provide some information or other insights regarding the determined cardiovascular health metric. Personalized insights may indicate aspects of collected physiological data (e.g., contributing factors within the physiological data) which were used to generate the determined cardiovascular health metric.

In some implementations, the system may be configured to receive user inputs regarding the determined cardiovascular health metric in order to train classifiers (e.g., supervised learning for a machine learning classifier) and improve cardiovascular health metric determination techniques. For example, the user device may receive user inputs 525, and these user inputs 525 may then be input into the classifier to train the classifier. In some cases, the PPG signal may be inputted into the machine learning classifier. In such cases, the system may determine the cardiovascular health metric in response to inputting the PPG signal into the machine learning classifier.

Figure 6:
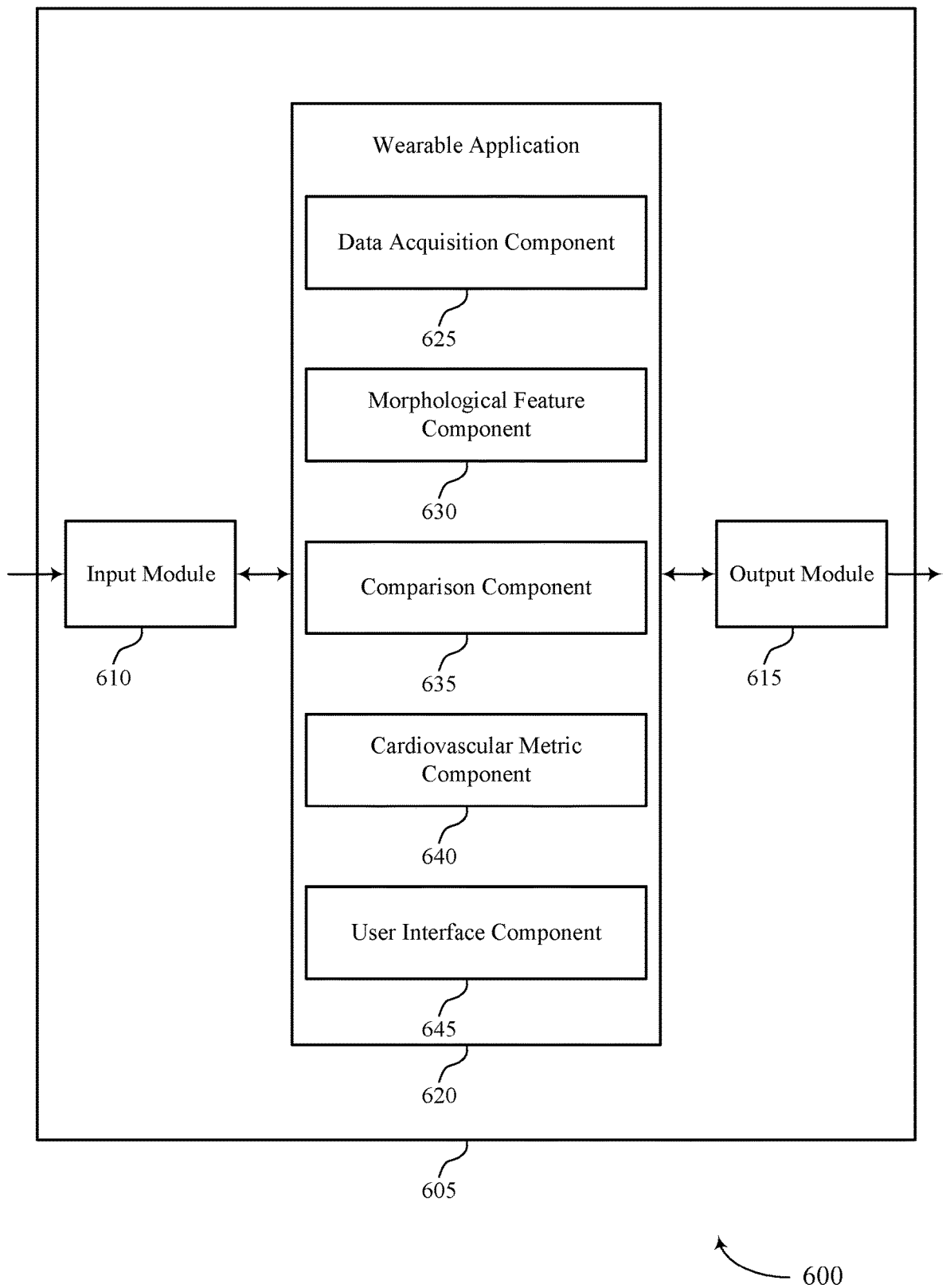
FIG. 6 shows a block diagram of an apparatus that supports cardiovascular health metric determination from wearable-based physiological data in accordance with aspects of the present disclosure.

FIG. 6 shows a block diagram 600 of a device 605 that supports cardiovascular health metric determination from wearable-based physiological data in accordance with aspects of the present disclosure. The device 605 may include an input module 610, an output module 615, and a wearable application 620. The device 605 may also include a processor. Each of these components may be in communication with one another (e.g., via one or more buses).

The input module 610 may provide a means for receiving information such as packets, user data, control information, or any combination thereof associated with various information channels (e.g., control channels, data channels, information channels related to illness detection techniques). Information may be passed on to other components of the device 605. The input module 610 may utilize a single antenna or a set of multiple antennas.

The output module 615 may provide a means for transmitting signals generated by other components of the device 605. For example, the output module 615 may transmit information such as packets, user data, control information, or any combination thereof associated with various information channels (e.g., control channels, data channels, information channels related to illness detection techniques). In some examples, the output module 615 may be co-located with the input module 610 in a transceiver module. The output module 615 may utilize a single antenna or a set of multiple antennas.

For example, the wearable application 620 may include a data acquisition component 625, a morphological feature component 630, a comparison component 635, a cardiovascular metric component 640, a user interface component 645, or any combination thereof. In some examples, the wearable application 620, or various components thereof, may be configured to perform various operations (e.g., receiving, monitoring, transmitting) using or otherwise in cooperation with the input module 610, the output module 615, or both. For example, the wearable application 620 may receive information from the input module 610, send information to the output module 615, or be integrated in combination with the input module 610, the output module 615, or both to receive information, transmit information, or perform various other operations as described herein.

The data acquisition component 625 may be configured as or otherwise support a means for receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle. The morphological feature component 630 may be configured as or otherwise support a means for extracting one or more morphological features related to a position of the first local maximum, a value of the downward slope, a degree of the curved feature, or a combination thereof. The comparison component 635 may be configured as or otherwise support a means for comparing the one or more morphological features with one or more features from a plurality of baseline PPG signal morphologies associated with a plurality of chronological ages based at least in part on extracting the one or more morphological features. The cardiovascular metric component 640 may be configured as or otherwise support a means for determining a cardiovascular health metric that indicates a cardiovascular health of the user relative to a chronological age of the user based at least in part on the comparison. The user interface component 645 may be configured as or otherwise support a means for causing a graphical user interface to display an indication of the cardiovascular health metric.

Figure 7:
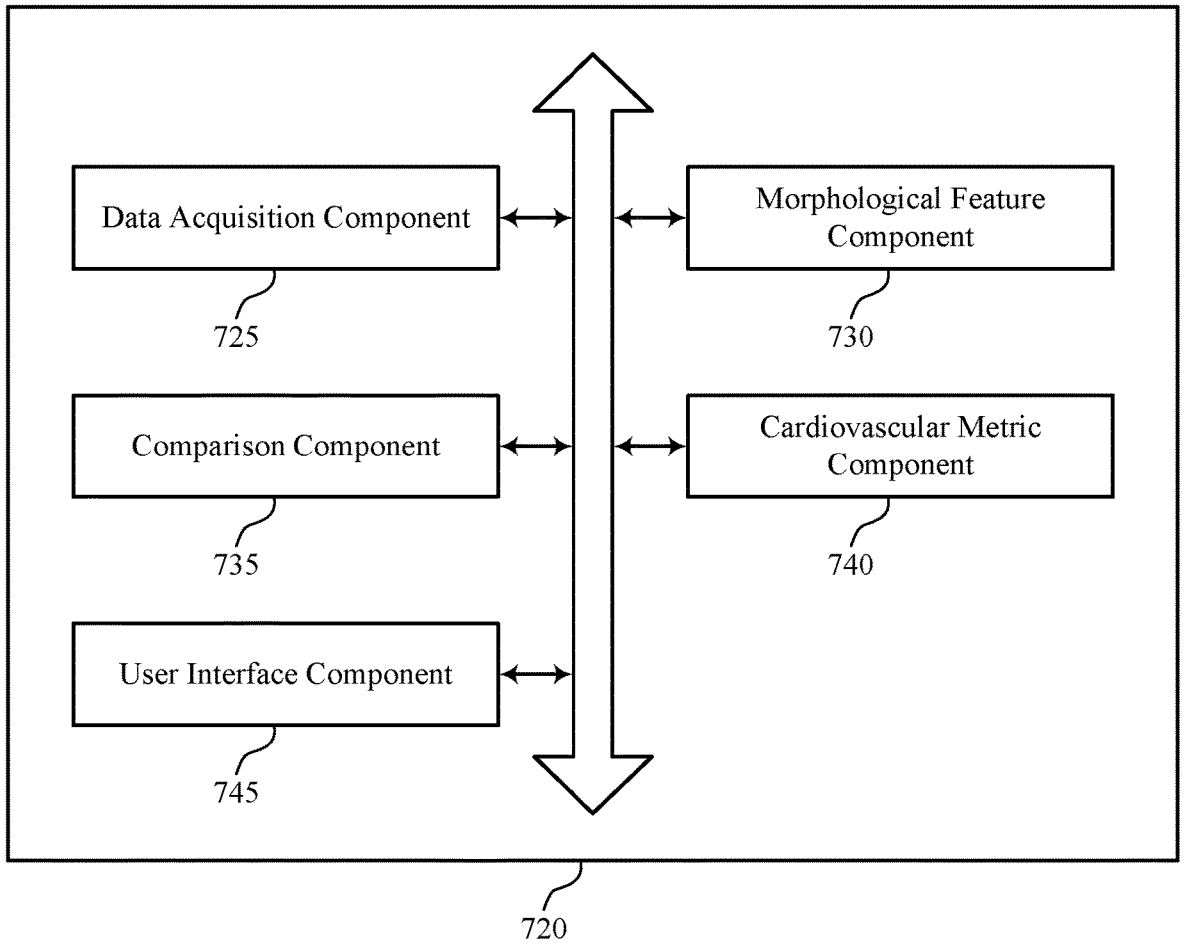
FIG. 7 shows a block diagram of a wearable application that supports cardiovascular health metric determination from wearable-based physiological data in accordance with aspects of the present disclosure.

FIG. 7 shows a block diagram 700 of a wearable application 720 that supports cardiovascular health metric determination from wearable-based physiological data in accordance with aspects of the present disclosure. The wearable application 720 may be an example of aspects of a wearable application or a wearable application 620, or both, as described herein. The wearable application 720, or various components thereof, may be an example of means for performing various aspects of cardiovascular health metric determination from wearable-based physiological data as described herein. For example, the wearable application 720 may include a data acquisition component 725, a morphological feature component 730, a comparison component 735, a cardiovascular metric component 740, a user interface component 745, or any combination thereof. Each of these components may communicate, directly or indirectly, with one another (e.g., via one or more buses).

The data acquisition component 725 may be configured as or otherwise support a means for receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle. The morphological feature component 730 may be configured as or otherwise support a means for extracting one or more morphological features related to a position of the first local maximum, a value of the downward slope, a degree of the curved feature, or a combination thereof. The comparison component 735 may be configured as or otherwise support a means for comparing the one or more morphological features with one or more features from a plurality of baseline PPG signal morphologies associated with a plurality of chronological ages based at least in part on extracting the one or more morphological features. The cardiovascular metric component 740 may be configured as or otherwise support a means for determining a cardiovascular health metric that indicates a cardiovascular health of the user relative to a chronological age of the user based at least in part on the comparison. The user interface component 745 may be configured as or otherwise support a means for causing a graphical user interface to display an indication of the cardiovascular health metric.

In some examples, to support extracting the one or more morphological features, the morphological feature component 730 may be configured as or otherwise support a means for computing a first derivative of the pulse waveform, a second derivative of the pulse waveform, or both. In some examples, to support extracting the one or more morphological features, the morphological feature component 730 may be configured as or otherwise support a means for identifying one or more local maximum or one or more local minimum of the first derivative of the pulse waveform or of the second derivative of the pulse waveform, or both, wherein the one or more morphological features are associated with the one or more local maximum or the one or more local minimum of the first derivative of the pulse waveform or of the second derivative of the pulse waveform, or both.

In some examples, to support extracting the one or more morphological features, the morphological feature component 730 may be configured as or otherwise support a means for determining an amplitude, the position, or both of the first local maximum, wherein the one or more morphological features are associated with the amplitude, the position, or both of the first local maximum.

In some examples, to support extracting the one or more morphological features, the morphological feature component 730 may be configured as or otherwise support a means for identifying a presence of a second local maximum of the pulse waveform, wherein the curved feature representative of the transition from the systolic phase to the diastolic phase of the cardiac cycle is associated with the second local maximum.

In some examples, to support extracting the one or more morphological features, the morphological feature component 730 may be configured as or otherwise support a means for identifying one or more positive slopes or one or more negative slopes of the pulse waveform, wherein the downward slope following the first local maximum is associated with the one or more negative slopes of the pulse waveform.

In some examples, the comparison component 735 may be configured as or otherwise support a means for determining which of the plurality of baseline PPG signal morphologies matches the one or more morphological features based at least in part on the comparison, wherein determining the cardiovascular health metric is based at least in part on the determination.

In some examples, the comparison component 735 may be configured as or otherwise support a means for computing a deviation in the one or more morphological features relative to the one or more features from a plurality of baseline PPG signal morphologies based at least in part on the comparison, wherein determining the cardiovascular health metric is based at least in part on computing the deviation.

In some examples, the data acquisition component 725 may be configured as or otherwise support a means for receiving, via a user device, an indication of data related to a health record of the user from the wearable device, physiological data from the wearable device, or both. In some examples, the cardiovascular metric component 740 may be configured as or otherwise support a means for adjusting the cardiovascular health metric based at least in part on receiving the indication, wherein causing the graphical user interface to display the indication is based at least in part on adjusting the cardiovascular health metric.

In some examples, the user interface component 745 may be configured as or otherwise support a means for causing a graphical user interface of a user device associated with the user to display a message associated with the cardiovascular health metric.

In some examples, the message further comprises recommendations to improve the cardiovascular health metric, trends associated with the cardiovascular health metric, educational content associated with the cardiovascular health metric, an adjusted set of activity targets, an adjusted set of sleep targets, or a combination thereof.

In some examples, the data acquisition component 725 may be configured as or otherwise support a means for identifying the plurality of baseline PPG signal morphologies associated with the plurality of chronological ages based at least in part on receiving the PPG signal, wherein the comparison is based at least in part on identifying the plurality of baseline PPG signal morphologies.

In some examples, the data acquisition component 725 may be configured as or otherwise support a means for inputting the PPG signal into a machine learning classifier, wherein determining the cardiovascular health metric is based at least in part on inputting the PPG signal into the machine learning classifier.

In some examples, the plurality of baseline PPG signal morphologies associated with the plurality of chronological ages are extracted from physiological data associated with multiple users.

In some examples, the wearable device comprises a wearable ring device.

In some examples, the wearable device collects physiological data from the user based on arterial blood flow, capillary blood flow, arteriole blood flow, or a combination thereof.

Figure 8:
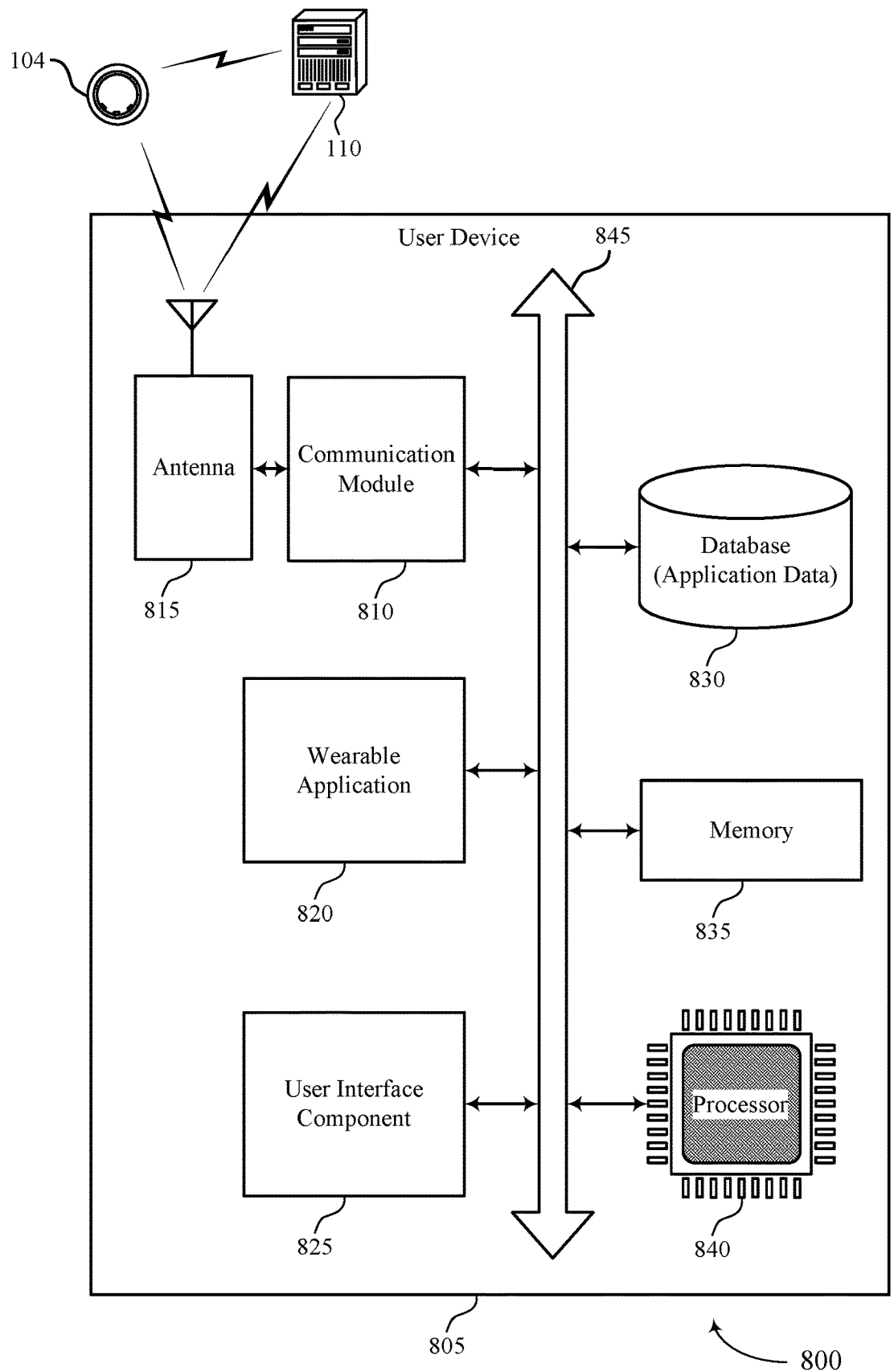
FIG. 8 shows a diagram of a system including a device that supports cardiovascular health metric determination from wearable-based physiological data in accordance with aspects of the present disclosure.

FIG. 8 shows a diagram of a system 800 including a device 805 that supports cardiovascular health metric determination from wearable-based physiological data in accordance with aspects of the present disclosure. The device 805 may be an example of or include the components of a device 605 as described herein. The device 805 may include an example of a user device 106, as described previously herein. The device 805 may include components for bi-directional communications including components for transmitting and receiving communications with a wearable device 104 and a server 110, such as a wearable application 820, a communication module 810, an antenna 815, a user interface component 825, a database (application data) 830, a memory 835, and a processor 840. These components may be in electronic communication or otherwise coupled (e.g., operatively, communicatively, functionally, electronically, electrically) via one or more buses (e.g., a bus 845).

The communication module 810 may manage input and output signals for the device 805 via the antenna 815. The communication module 810 may include an example of the communication module 220-*b* of the user device 106 shown and described in FIG. 2. In this regard, the communication module 810 may manage communications with the ring 104 and the server 110, as illustrated in FIG. 2. The communication module 810 may also manage peripherals not integrated into the device 805. In some cases, the communication module 810 may represent a physical connection or port to an external peripheral. In some cases, the communication module 810 may utilize an operating system such as iOS®, ANDROID®, MS-DOS®, MS-WINDOWS®, OS/2®, UNIX®, LINUX®, or another known operating system. In other cases, the communication module 810 may represent or interact with a wearable device (e.g., ring 104), modem, a keyboard, a mouse, a touchscreen, or a similar device. In some cases, the communication module 810 may be implemented as part of the processor 840. In some examples, a user may interact with the device 805 via the communication module 810, user interface component 825, or via hardware components controlled by the communication module 810.

In some cases, the device 805 may include a single antenna 815. However, in some other cases, the device 805 may have more than one antenna 815, which may be capable of concurrently transmitting or receiving multiple wireless transmissions. The communication module 810 may communicate bi-directionally, via the one or more antennas 815, wired, or wireless links as described herein. For example, the communication module 810 may represent a wireless transceiver and may communicate bi-directionally with another wireless transceiver. The communication module 810 may also include a modem to modulate the packets, to provide the modulated packets to one or more antennas 815 for transmission, and to demodulate packets received from the one or more antennas 815.

The user interface component 825 may manage data storage and processing in a database 830. In some cases, a user may interact with the user interface component 825. In other cases, the user interface component 825 may operate automatically without user interaction. The database 830 may be an example of a single database, a distributed database, multiple distributed databases, a data store, a data lake, or an emergency backup database.

The memory 835 may include RAM and ROM. The memory 835 may store computer-readable, computer-executable software including instructions that, when executed, cause the processor 840 to perform various functions described herein. In some cases, the memory 835 may contain, among other things, a BIOS which may control basic hardware or software operation such as the interaction with peripheral components or devices.

The processor 840 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 840 may be configured to operate a memory array using a memory controller. In other cases, a memory controller may be integrated into the processor 840. The processor 840 may be configured to execute computer-readable instructions stored in a memory 835 to perform various functions (e.g., functions or tasks supporting a method and system for sleep staging algorithms).

For example, the wearable application 820 may be configured as or otherwise support a means for receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle. The wearable application 820 may be configured as or otherwise support a means for extracting one or more morphological features related to a position of the first local maximum, a value of the downward slope, a degree of the curved feature, or a combination thereof. The wearable application 820 may be configured as or otherwise support a means for comparing the one or more morphological features with one or more features from a plurality of baseline PPG signal morphologies associated with a plurality of chronological ages based at least in part on extracting the one or more morphological features. The wearable application 820 may be configured as or otherwise support a means for determining a cardiovascular health metric that indicates a cardiovascular health of the user relative to a chronological age of the user based at least in part on the comparison. The wearable application 820 may be configured as or otherwise support a means for causing a graphical user interface to display an indication of the cardiovascular health metric.

By including or configuring the wearable application 820 in accordance with examples as described herein, the device 805 may support techniques for improved communication reliability, reduced latency, improved user experience related to reduced processing, reduced power consumption, more efficient utilization of communication resources, improved coordination between devices, longer battery life, improved utilization of processing capability, or a combination thereof.

The wearable application 820 may include an application (e.g., "app"), program, software, or other component which is configured to facilitate communications with a ring 104, server 110, other user devices 106, and the like. For example, the wearable application 820 may include an application executable on a user device 106 which is configured to receive data (e.g., physiological data) from a ring 104, perform processing operations on the received data, transmit and receive data with the servers 110, and cause presentation of data to a user 102.

Figure 9:
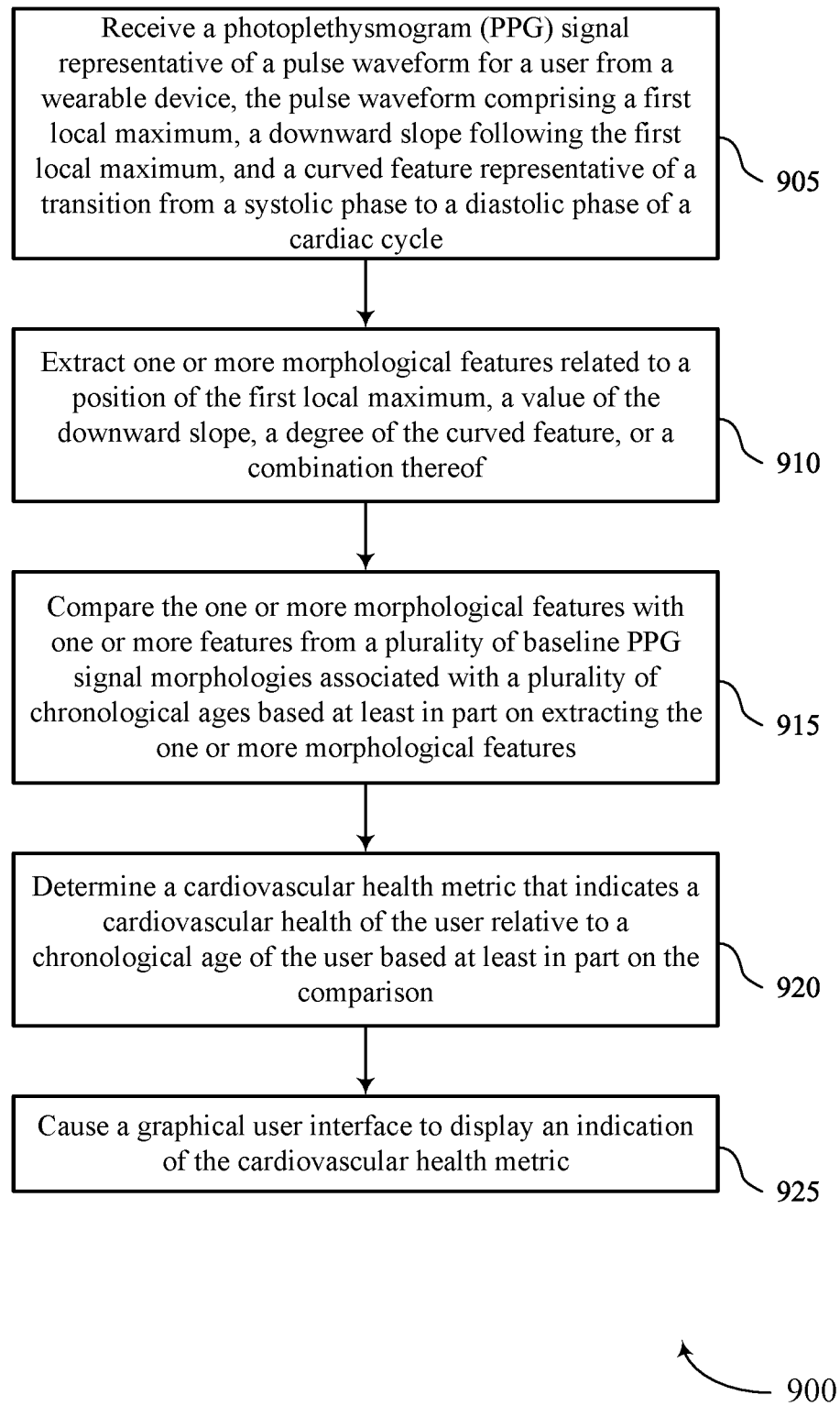
FIGS. 9 through 11 show flowcharts illustrating methods that support cardiovascular health metric determination from wearable-based physiological data in accordance with aspects of the present disclosure.

FIG. 9 shows a flowchart illustrating a method 900 that supports cardiovascular health metric determination from wearable-based physiological data in accordance with aspects of the present disclosure. The operations of the method 900 may be implemented by a user device or its components as described herein. For example, the operations of the method 900 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 905, the method may include receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle. The operations of 905 may be performed in accordance with examples as disclosed herein. In some examples, aspects of the operations of 905 may be performed by a data acquisition component 725 as described with reference to FIG. 7.

At 910, the method may include extracting one or more morphological features related to a position of the first local maximum, a value of the downward slope, a degree of the curved feature, or a combination thereof. The operations of 910 may be performed in accordance with examples as disclosed herein. In some examples, aspects of the operations of 910 may be performed by a morphological feature component 730 as described with reference to FIG. 7.

At 915, the method may include comparing the one or more morphological features with one or more features from a plurality of baseline PPG signal morphologies associated with a plurality of chronological ages based at least in part on extracting the one or more morphological features. The operations of 915 may be performed in accordance with examples as disclosed herein. In some examples, aspects of the operations of 915 may be performed by a comparison component 735 as described with reference to FIG. 7.

At 920, the method may include determining a cardiovascular health metric that indicates a cardiovascular health of the user relative to a chronological age of the user based at least in part on the comparison. The operations of 920 may be performed in accordance with examples as disclosed herein. In some examples, aspects of the operations of 920 may be performed by a cardiovascular metric component 740 as described with reference to FIG. 7.

At 925, the method may include causing a graphical user interface to display an indication of the cardiovascular health metric. The operations of 925 may be performed in accordance with examples as disclosed herein. In some examples, aspects of the operations of 925 may be performed by a user interface component 745 as described with reference to FIG. 7.

Figure 10:
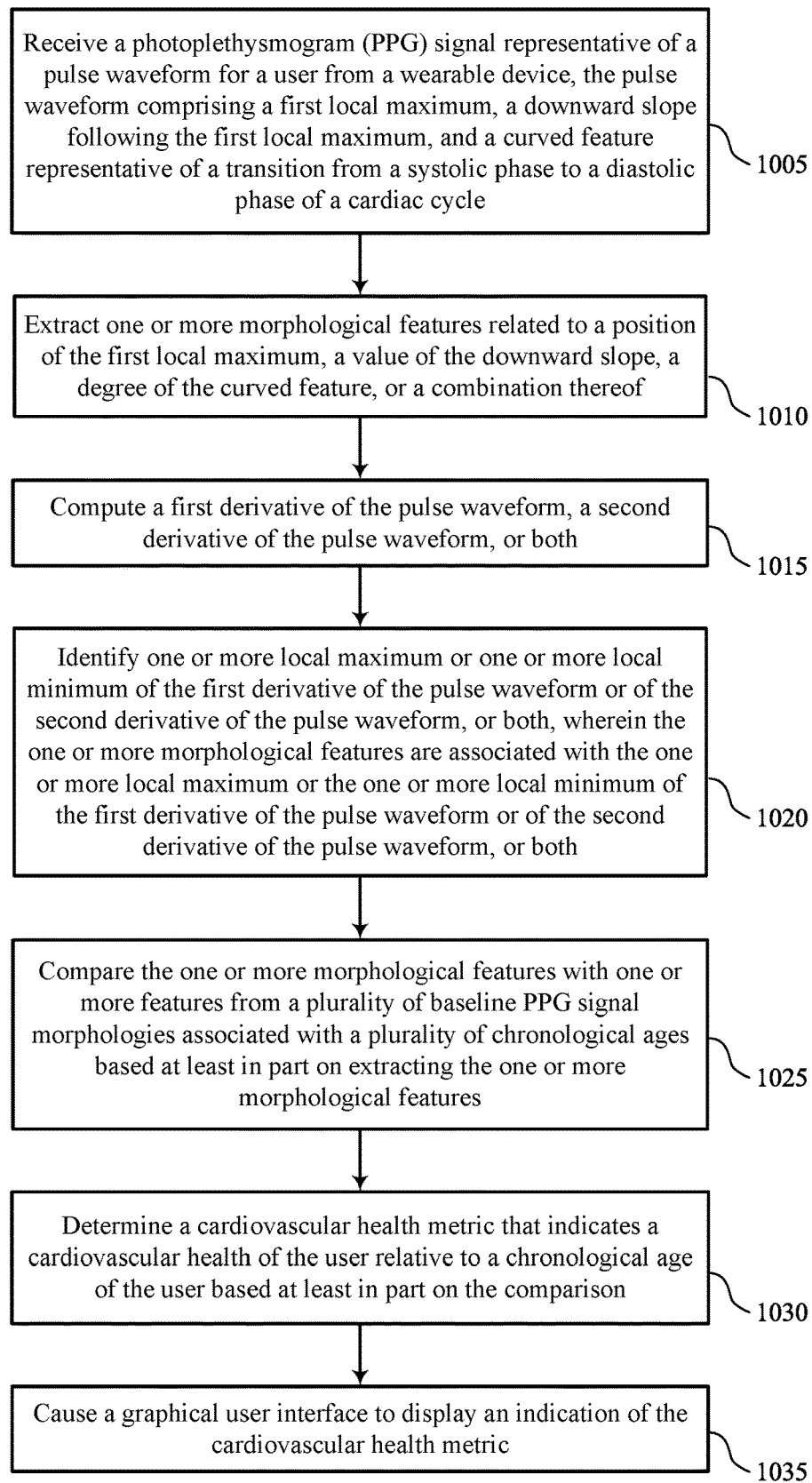

FIG. 10 shows a flowchart illustrating a method 1000 that supports cardiovascular health metric determination from wearable-based physiological data in accordance with aspects of the present disclosure. The operations of the method 1000 may be implemented by a user device or its components as described herein. For example, the operations of the method 1000 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1005, the method may include receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle. The operations of 1005 may be performed in accordance with examples as disclosed herein. In some examples, aspects of the operations of 1005 may be performed by a data acquisition component 725 as described with reference to FIG. 7.

At 1010, the method may include extracting one or more morphological features related to a position of the first local maximum, a value of the downward slope, a degree of the curved feature, or a combination thereof. The operations of 1010 may be performed in accordance with examples as disclosed herein. In some examples, aspects of the operations of 1010 may be performed by a morphological feature component 730 as described with reference to FIG. 7.

At 1015, the method may include computing a first derivative of the pulse waveform, a second derivative of the pulse waveform, or both. The operations of 1015 may be performed in accordance with examples as disclosed herein. In some examples, aspects of the operations of 1015 may be performed by a morphological feature component 730 as described with reference to FIG. 7.

At 1020, the method may include identifying one or more local maximum or one or more local minimum of the first derivative of the pulse waveform or of the second derivative of the pulse waveform, or both, wherein the one or more morphological features are associated with the one or more local maximum or the one or more local minimum of the first derivative of the pulse waveform or of the second derivative of the pulse waveform, or both. The operations of 1020 may be performed in accordance with examples as disclosed herein. In some examples, aspects of the operations of 1020 may be performed by a morphological feature component 730 as described with reference to FIG. 7.

At 1025, the method may include comparing the one or more morphological features with one or more features from a plurality of baseline PPG signal morphologies associated with a plurality of chronological ages based at least in part on extracting the one or more morphological features. The operations of 1025 may be performed in accordance with examples as disclosed herein. In some examples, aspects of the operations of 1025 may be performed by a comparison component 735 as described with reference to FIG. 7.

At 1030, the method may include determining a cardiovascular health metric that indicates a cardiovascular health of the user relative to a chronological age of the user based at least in part on the comparison. The operations of 1030 may be performed in accordance with examples as disclosed herein. In some examples, aspects of the operations of 1030 may be performed by a cardiovascular metric component 740 as described with reference to FIG. 7.

At 1035, the method may include causing a graphical user interface to display an indication of the cardiovascular health metric. The operations of 1035 may be performed in accordance with examples as disclosed herein. In some examples, aspects of the operations of 1035 may be performed by a user interface component 745 as described with reference to FIG. 7.

Figure 11:
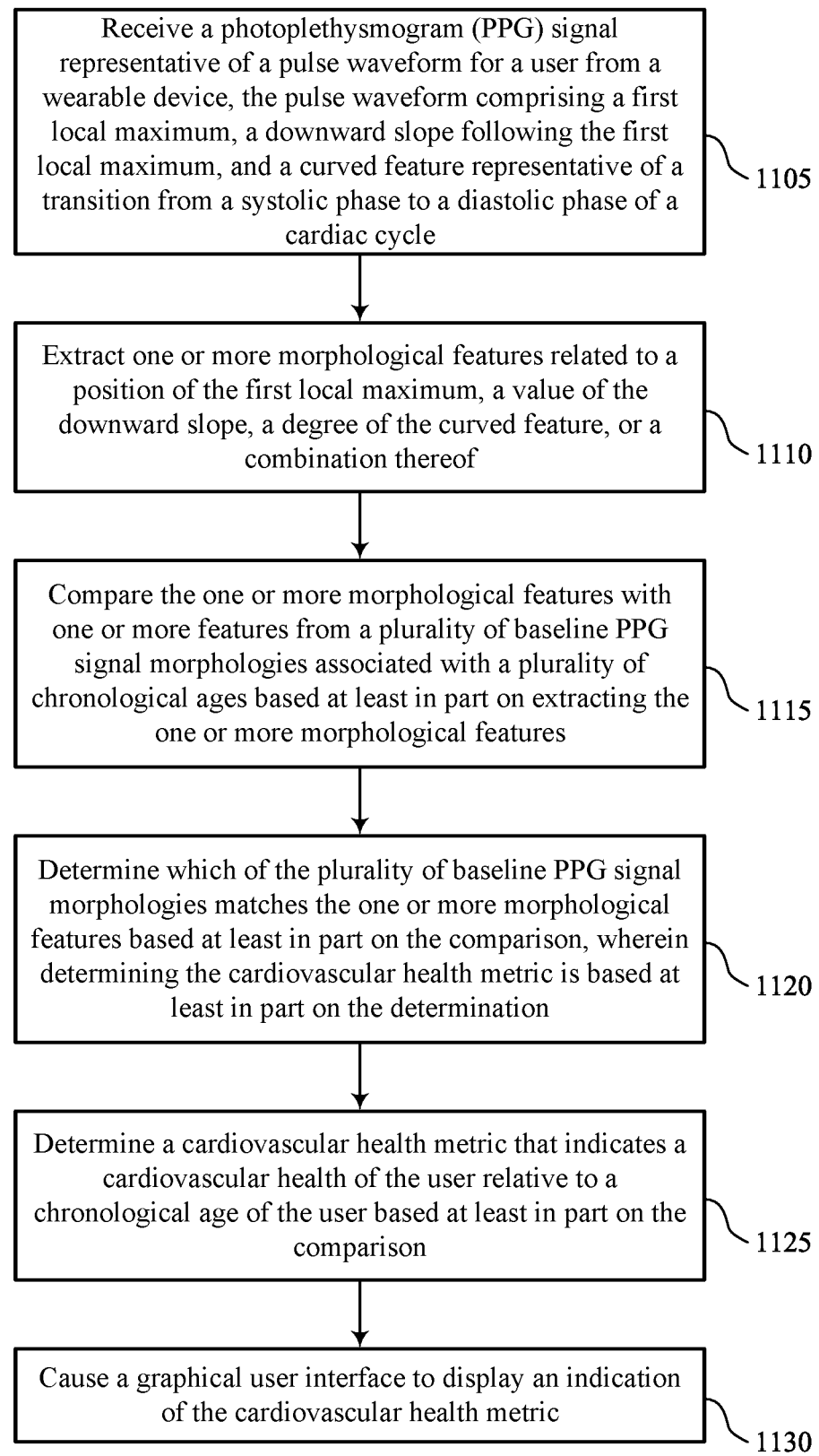

FIG. 11 shows a flowchart illustrating a method 1100 that supports cardiovascular health metric determination from wearable-based physiological data in accordance with aspects of the present disclosure. The operations of the method 1100 may be implemented by a user device or its components as described herein. For example, the operations of the method 1100 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1105, the method may include receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle. The operations of 1105 may be performed in accordance with examples as disclosed herein. In some examples, aspects of the operations of 1105 may be performed by a data acquisition component 725 as described with reference to FIG. 7.

At 1110, the method may include extracting one or more morphological features related to a position of the first local maximum, a value of the downward slope, a degree of the curved feature, or a combination thereof. The operations of 1110 may be performed in accordance with examples as disclosed herein. In some examples, aspects of the operations of 1110 may be performed by a morphological feature component 730 as described with reference to FIG. 7.

At 1115, the method may include comparing the one or more morphological features with one or more features from a plurality of baseline PPG signal morphologies associated with a plurality of chronological ages based at least in part on extracting the one or more morphological features. The operations of 1115 may be performed in accordance with examples as disclosed herein. In some examples, aspects of the operations of 1115 may be performed by a comparison component 735 as described with reference to FIG. 7.

At 1120, the method may include determining which of the plurality of baseline PPG signal morphologies matches the one or more morphological features based at least in part on the comparison, wherein determining the cardiovascular health metric is based at least in part on the determination. The operations of 1120 may be performed in accordance with examples as disclosed herein. In some examples, aspects of the operations of 1120 may be performed by a comparison component 735 as described with reference to FIG. 7.

At 1125, the method may include determining a cardiovascular health metric that indicates a cardiovascular health of the user relative to a chronological age of the user based at least in part on the comparison. The operations of 1125 may be performed in accordance with examples as disclosed herein. In some examples, aspects of the operations of 1125 may be performed by a cardiovascular metric component 740 as described with reference to FIG. 7.

At 1130, the method may include causing a graphical user interface to display an indication of the cardiovascular health metric. The operations of 1130 may be performed in accordance with examples as disclosed herein. In some examples, aspects of the operations of 1130 may be performed by a user interface component 745 as described with reference to FIG. 7.

It should be noted that the methods described above describe possible implementations, and that the operations and the steps may be rearranged or otherwise modified and that other implementations are possible. Furthermore, aspects from two or more of the methods may be combined.

A method is described. The method may include receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle, extracting one or more morphological features related to a position of the first local maximum, a value of the downward slope, a degree of the curved feature, or a combination thereof, comparing the one or more morphological features with one or more features from a plurality of baseline PPG signal morphologies associated with a plurality of chronological ages based at least in part on extracting the one or more morphological features, determining a cardiovascular health metric that indicates a cardiovascular health of the user relative to a chronological age of the user based at least in part on the comparison, and causing a graphical user interface to display an indication of the cardiovascular health metric.

An apparatus is described. The apparatus may include a processor, memory coupled with the processor, and instructions stored in the memory. The instructions may be executable by the processor to cause the apparatus to receive a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle, extract one or more morphological features related to a position of the first local maximum, a value of the downward slope, a degree of the curved feature, or a combination thereof, compare the one or more morphological features with one or more features from a plurality of baseline PPG signal morphologies associated with a plurality of chronological ages based at least in part on extracting the one or more morphological features, determine a cardiovascular health metric that indicates a cardiovascular health of the user relative to a chronological age of the user based at least in part on the comparison, and cause a graphical user interface to display an indication of the cardiovascular health metric.

Another apparatus is described. The apparatus may include means for receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle, means for extracting one or more morphological features related to a position of the first local maximum, a value of the downward slope, a degree of the curved feature, or a combination thereof, means for comparing the one or more morphological features with one or more features from a plurality of baseline PPG signal morphologies associated with a plurality of chronological ages based at least in part on extracting the one or more morphological features, means for determining a cardiovascular health metric that indicates a cardiovascular health of the user relative to a chronological age of the user based at least in part on the comparison, and means for causing a graphical user interface to display an indication of the cardiovascular health metric.

A non-transitory computer-readable medium storing code is described. The code may include instructions executable by a processor to receive a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle, extract one or more morphological features related to a position of the first local maximum, a value of the downward slope, a degree of the curved feature, or a combination thereof, compare the one or more morphological features with one or more features from a plurality of baseline PPG signal morphologies associated with a plurality of chronological ages based at least in part on extracting the one or more morphological features, determine a cardiovascular health metric that indicates a cardiovascular health of the user relative to a chronological age of the user based at least in part on the comparison, and cause a graphical user interface to display an indication of the cardiovascular health metric.

In some examples of the method, apparatuses, and non-transitory computer-readable medium described herein, extracting the one or more morphological features may include operations, features, means, or instructions for computing a first derivative of the pulse waveform, a second derivative of the pulse waveform, or both and identifying one or more local maximum or one or more local minimum of the first derivative of the pulse waveform or of the second derivative of the pulse waveform, or both, wherein the one or more morphological features may be associated with the one or more local maximum or the one or more local minimum of the first derivative of the pulse waveform or of the second derivative of the pulse waveform, or both.

In some examples of the method, apparatuses, and non-transitory computer-readable medium described herein, extracting the one or more morphological features may include operations, features, means, or instructions for determining an amplitude, the position, or both of the first local maximum, wherein the one or more morphological features may be associated with the amplitude, the position, or both of the first local maximum.

In some examples of the method, apparatuses, and non-transitory computer-readable medium described herein, extracting the one or more morphological features may include operations, features, means, or instructions for identifying a presence of a second local maximum of the pulse waveform, wherein the curved feature representative of the transition from the systolic phase to the diastolic phase of the cardiac cycle may be associated with the second local maximum.

In some examples of the method, apparatuses, and non-transitory computer-readable medium described herein, extracting the one or more morphological features may include operations, features, means, or instructions for identifying one or more positive slopes or one or more negative slopes of the pulse waveform, wherein the downward slope following the first local maximum may be associated with the one or more negative slopes of the pulse waveform.

Some examples of the method, apparatuses, and non-transitory computer-readable medium described herein may further include operations, features, means, or instructions for determining which of the plurality of baseline PPG signal morphologies matches the one or more morphological features based at least in part on the comparison, wherein determining the cardiovascular health metric may be based at least in part on the determination.

Some examples of the method, apparatuses, and non-transitory computer-readable medium described herein may further include operations, features, means, or instructions for computing a deviation in the one or more morphological features relative to the one or more features from a plurality of baseline PPG signal morphologies based at least in part on the comparison, wherein determining the cardiovascular health metric may be based at least in part on computing the deviation.

Some examples of the method, apparatuses, and non-transitory computer-readable medium described herein may further include operations, features, means, or instructions for receiving, via a user device, an indication of data related to a health record of the user from the wearable device, physiological data from the wearable device, or both and adjusting the cardiovascular health metric based at least in part on receiving the indication, wherein causing the graphical user interface to display the indication may be based at least in part on adjusting the cardiovascular health metric.

Some examples of the method, apparatuses, and non-transitory computer-readable medium described herein may further include operations, features, means, or instructions for causing a graphical user interface of a user device associated with the user to display a message associated with the cardiovascular health metric.

In some examples of the method, apparatuses, and non-transitory computer-readable medium described herein, the message further comprises recommendations to improve the cardiovascular health metric, trends associated with the cardiovascular health metric, educational content associated with the cardiovascular health metric, an adjusted set of activity targets, an adjusted set of sleep targets, or a combination thereof.

Some examples of the method, apparatuses, and non-transitory computer-readable medium described herein may further include operations, features, means, or instructions for identifying the plurality of baseline PPG signal morphologies associated with the plurality of chronological ages based at least in part on receiving the PPG signal, wherein the comparison may be based at least in part on identifying the plurality of baseline PPG signal morphologies.

Some examples of the method, apparatuses, and non-transitory computer-readable medium described herein may further include operations, features, means, or instructions for inputting the PPG signal into a machine learning classifier, wherein determining the cardiovascular health metric may be based at least in part on inputting the PPG signal into the machine learning classifier.

In some examples of the method, apparatuses, and non-transitory computer-readable medium described herein, the plurality of baseline PPG signal morphologies associated with the plurality of chronological ages may be extracted from physiological data associated with multiple users.

In some examples of the method, apparatuses, and non-transitory computer-readable medium described herein, the wearable device comprises a wearable ring device.

In some examples of the method, apparatuses, and non-transitory computer-readable medium described herein, the wearable device collects physiological data from the user based on arterial blood flow, capillary blood flow, arteriole blood flow, or a combination thereof.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method comprising:
   receiving a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle;
   extracting a plurality of morphological features related to a position of the first local maximum, a value of the downward slope, a degree of the curved feature, or a combination thereof;
   comparing, based at least in part on extracting the plurality of morphological features, the plurality of extracted morphological features with a plurality of baseline morphological features of a plurality of baseline pulse waveforms, wherein each baseline pulse waveform of the plurality of baseline pulse waveforms is associated with a different chronological age of a plurality of chronological ages;
   identifying a first baseline pulse waveform from the plurality of baseline pulse waveforms based at least in part on matching the plurality of extracted morphological features to a first plurality of baseline morphological features associated with the first baseline pulse waveform, wherein the first baseline pulse waveform is associated with a first chronological age of the plurality of chronological ages;
   determining a cardiovascular health metric that indicates a cardiovascular health of the user relative to a chronological age of the user based at least in part on a difference between the chronological age of the user and the first chronological age associated with the first baseline pulse waveform; and
   causing a graphical user interface to display an indication of the cardiovascular health metric.

2. The method of claim 1, wherein extracting the plurality of morphological features further comprises:
   computing a first derivative of the pulse waveform, a second derivative of the pulse waveform, or both; and
   identifying one or more local maximum or one or more local minimum of the first derivative of the pulse waveform or of the second derivative of the pulse waveform, or both, wherein the plurality of extracted morphological features are associated with the one or more local maximum or the one or more local minimum of the first derivative of the pulse waveform or of the second derivative of the pulse waveform, or both.

3. The method of claim 1, wherein extracting the plurality of morphological features further comprises:
   determining an amplitude, the position, or both of the first local maximum, wherein the plurality of extracted morphological features are associated with the amplitude, the position, or both of the first local maximum.

4. The method of claim 1, wherein extracting the plurality of morphological features further comprises:
   identifying a presence of a second local maximum of the pulse waveform, wherein the curved feature representative of the transition from the systolic phase to the diastolic phase of the cardiac cycle is associated with the second local maximum.

5. The method of claim 1, wherein extracting the plurality of morphological features further comprises:
   identifying one or more positive slopes or one or more negative slopes of the pulse waveform, wherein the downward slope following the first local maximum is associated with the one or more negative slopes of the pulse waveform.

6. The method of claim 1, further comprising:
computing a deviation in the plurality of extracted morphological features relative to the first plurality of baseline morphological features associated with the first baseline pulse waveform, wherein matching the plurality of extracted morphological features to the first plurality of baseline morphological features is based at least in part on computing the deviation.

7. The method of claim 1, further comprising:
receiving, via a user device, an indication of data related to a health record of the user from the wearable device, physiological data from the wearable device, or both; and
adjusting the cardiovascular health metric based at least in part on receiving the indication, wherein causing the graphical user interface to display the indication is based at least in part on adjusting the cardiovascular health metric.

8. The method of claim 1, further comprising:
causing the graphical user interface of a user device associated with the user to display a message associated with the cardiovascular health metric.

9. The method of claim 8, wherein the message further comprises recommendations to improve the cardiovascular health metric, trends associated with the cardiovascular health metric, educational content associated with the cardiovascular health metric, an adjusted set of activity targets, an adjusted set of sleep targets, or a combination thereof.

10. The method of claim 1, further comprising:
identifying the plurality of baseline pulse waveforms associated with the plurality of chronological ages based at least in part on receiving the PPG signal, wherein the comparison is based at least in part on identifying the plurality of baseline pulse waveforms.

11. The method of claim 1, further comprising:
inputting the PPG signal into a machine learning classifier, wherein determining the cardiovascular health metric is based at least in part on inputting the PPG signal into the machine learning classifier.

12. The method of claim 1, wherein the plurality of baseline pulse waveforms associated with the plurality of chronological ages are extracted from physiological data associated with multiple users.

13. The method of claim 1, wherein the wearable device comprises a wearable ring device.

14. The method of claim 1, wherein the wearable device collects physiological data from the user based on arterial blood flow, capillary blood flow, arteriole blood flow, or a combination thereof.

15. An apparatus, comprising:
a processor;
memory coupled with the processor; and
instructions stored in the memory and executable by the processor to cause the apparatus to:
receive a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle;
extract a plurality of morphological features related to a position of the first local maximum, a value of the downward slope, a degree of the curved feature, or a combination thereof;
compare, based at least in part on extracting the plurality of morphological features, the plurality of extracted morphological features with a plurality of baseline morphological features of a plurality of baseline pulse waveforms, wherein each baseline pulse waveform of the plurality of baseline pulse waveforms is associated with a different chronological age of a plurality of chronological ages;
identify a first baseline pulse waveform from the plurality of baseline pulse waveforms based at least in part on matching the plurality of extracted morphological features to a first plurality of baseline morphological features associated with the first baseline pulse waveform, wherein the first baseline pulse waveform is associated with a first chronological age of the plurality of chronological ages;
determine a cardiovascular health metric that indicates a cardiovascular health of the user relative to a chronological age of the user based at least in part on a difference between the chronological age of the user and the first chronological age associated with the first baseline pulse waveform; and
cause a graphical user interface to display an indication of the cardiovascular health metric.

16. The apparatus of claim 15, wherein the instructions to extract the plurality of morphological features are further executable by the processor to cause the apparatus to:
compute a first derivative of the pulse waveform, a second derivative of the pulse waveform, or both; and
identify one or more local maximum or one or more local minimum of the first derivative of the pulse waveform or of the second derivative of the pulse waveform, or both, wherein the plurality of extracted morphological features are associated with the one or more local maximum or the one or more local minimum of the first derivative of the pulse waveform or of the second derivative of the pulse waveform, or both.

17. The apparatus of claim 15, wherein the instructions to extract the plurality of morphological features are further executable by the processor to cause the apparatus to:
determine an amplitude, the position, or both of the first local maximum, wherein the plurality of extracted morphological features are associated with the amplitude, the position, or both of the first local maximum.

18. A non-transitory computer-readable medium storing code, the code comprising instructions executable by a processor to:
receive a photoplethysmogram (PPG) signal representative of a pulse waveform for a user from a wearable device, the pulse waveform comprising a first local maximum, a downward slope following the first local maximum, and a curved feature representative of a transition from a systolic phase to a diastolic phase of a cardiac cycle;
extract a plurality of morphological features related to a position of the first local maximum, a value of the downward slope, a degree of the curved feature, or a combination thereof;
compare, based at least in part on extracting the plurality of morphological features, the plurality of extracted morphological features with a plurality of baseline morphological features of a plurality of baseline pulse waveforms, wherein each baseline pulse waveform of the plurality of baseline pulse waveforms is associated with a different chronological age of a plurality of chronological ages;
identify a first baseline pulse waveform from the plurality of baseline pulse waveforms based at least in part on matching the plurality of extracted morphological features to a first plurality of baseline morphological features associated with the first baseline pulse waveform, wherein the first baseline pulse waveform is associated with a first chronological age of the plurality of chronological ages;

determine a cardiovascular health metric that indicates a cardiovascular health of the user relative to a chronological age of the user based at least in part on a difference between the chronological age of the user and the first chronological age associated with the first baseline pulse waveform; and cause a graphical user interface to display an indication of the cardiovascular health metric.

19. The non-transitory computer-readable medium of claim 18, wherein the instructions to extract the plurality of morphological features are further executable by the processor to:

compute a first derivative of the pulse waveform, a second derivative of the pulse waveform, or both; and identify one or more local maximum or one or more local minimum of the first derivative of the pulse waveform or of the second derivative of the pulse waveform, or both, wherein the plurality of extracted morphological features are associated with the one or more local maximum or the one or more local minimum of the first derivative of the pulse waveform or of the second derivative of the pulse waveform, or both.

* * * * *